United States Patent
Csete et al.

(10) Patent No.: US 6,610,540 B1
(45) Date of Patent: Aug. 26, 2003

(54) LOW OXYGEN CULTURING OF CENTRAL NERVOUS SYSTEM PROGENITOR CELLS

(75) Inventors: Marie Csete, Ann Arbor, MI (US); John Doyle, South Pasadena, CA (US); Barbara J. Wold, San Marino, CA (US); Ron McKay, Bethesda, MD (US); Lorenz Studer, New York, NY (US)

(73) Assignees: California Institute of Technology, Pasadena, CA (US); National Institutes of Health, Bethesda, MD (US)

( * ) Notice: Subject to any disclaimer, the term of this patent is extended or adjusted under 35 U.S.C. 154(b) by 0 days.

(21) Appl. No.: 09/425,462

(22) Filed: Oct. 22, 1999

Related U.S. Application Data

(63) Continuation-in-part of application No. 09/195,569, filed on Nov. 18, 1998, now Pat. No. 6,184,035.

(51) Int. Cl.$^7$ .............................. C12N 5/00; C12N 5/02; C12N 5/06; C12N 5/08

(52) U.S. Cl. ........................... 435/375; 435/4; 435/325; 435/377; 435/352; 435/368

(58) Field of Search ........................... 435/4, 325, 352, 435/366, 368, 375, 377, 363, 383; 530/350, 300

(56) References Cited

U.S. PATENT DOCUMENTS

| | | | |
|---|---|---|---|
| 5,328,695 A | | 7/1994 | Lucas et al. ................. 424/426 |
| 5,550,050 A | | 8/1996 | Holland et al. ........... 435/240.2 |
| 5,728,581 A | | 3/1998 | Schwartz et al. ............ 435/385 |
| 5,750,103 A | | 5/1998 | Cherksey ................. 424/93.21 |
| 5,750,376 A | * | 5/1998 | Weiss et al. ............. 435/69.52 |
| 6,165,783 A | * | 12/2000 | Weiss et al. ................ 435/325 |
| 6,184,035 B1 | | 2/2001 | Csete et al. ................. 435/377 |

OTHER PUBLICATIONS

Davis et al. Examining pattern formation in mouse, chicken, and frog embryos with an En–specific antiserum. Development 111: 287–298, 1991.*

Davis et al. Expression patterns of the homeo box–containg genes En–1 and En–2 and the proto–oncogene int–1 diverge during mouse development. Genes and Development 2: 1736–1744, 1988.*

Hynes et al. Specification of dopaminergic and serotonergic neurons in the vertebrate CNS. Curr Opin Neurobiol 9: 26–36, 1999.*

Studer et al. Enhanced proliferation, survival, and dopaminergic differentiation of CNS precursors in lowered oxygen. J Neurosci 20(19): 7377–7383, 2000.*

Wenner et al. Topographical and physiological characterization of interneurons that express engrailed–1 in the embryonic chick spinal cord. J Neurophysiol 84: 2651–2657, 2000.*

Ye et al. FGF and Shh signals control dopaminergic and serotonergic cell fate in the anterior nerual plate. Cell 93: 755–766, 1998.*

Zec et al. Expression of the homeobox–containing genes EN1 and EN2 in the human fetal midgestational medulla and cerebellum. J. Neuropathol and Exp Neurol 56(3): 236–242, 1997.*

Simon et al. Fate of midbrain dopaminergic neurons controlled by the engrailed genes. J. Neurosci 21(9): 3126–3134, 2001.*

Wong et al. Comparison of growth rates of bovine retinal and brain microvascular pericytes in different oxygen concentrations in vitro. Aust. New Zeal. J. Opthalm. 23(4): 299–308, 1995.*

Yun et al. Cellular adaptive response to low oxygen tension: apoptosis and resistance. Neurochem Res 22(4): 517–522, 1997.*

Storch, T. Oxygen concentration regulates 5–azacytidine–induced myogenesis in C3H/10T1/2 cultures. Biochim. Biophys. Acta 1055: 126–129, 1990.*

Iván J. Sosa, M.D. et al., "Isolation and Long–term Survival of Adult Human Sensory Neurons In Vitro," *Neurosurgery*, Vol. 42, No. 3, Mar. 1998, pp. 681–686.

R. A. Metcalfe et al., "Stimulation of extraocular muscle fibroblasts by cytokines and hypoxia: possible role in thyroid–associated ophthalmopathy," *Clinical Endocrinology* 40, 1994, pp. 67–72.

Eugene D. Robin et al., "Coordinate Regulation of Glycolysis by Hypoxia in Mammalian Cells," *Journal of Cellular Physiology*, 118, 1984, pp. 287–290.

N.V. Darinskii et al., "Effect of the Conditions of Antenatal Development on Functional Maturation of Rabbit Fetal Skeletal Muscle," *Bulletin of Experimental Biology and Medicine*, vol. 77, No. 2, Feb. 1974, pp. 104–106.

(List continued on next page.)

Primary Examiner—Elizabeth Kemmerer
Assistant Examiner—Bridget E. Bunner
(74) Attorney, Agent, or Firm—Brinks Hofer Gilson & Lione

(57) ABSTRACT

The present invention relates to the growth of cells in culture under conditions that promote cell survival, proliferation, and/or cellular differentiation. The present inventors have found that proliferation was promoted and apoptosis reduced when cells were grown in lowered oxygen as compared to environmental oxygen conditions traditionally employed in cell culture techniques. Further, the inventors found that differentiation of precursor cells to specific fates also was enhanced in lowered oxygen where a much greater number and fraction of dopaminergic neurons were obtained when mesencephalic precursors were expanded and differentiated in lowered oxygen conditions. Thus at more physiological oxygen levels the proliferation and differentiation of CNS precursors is enhanced, and lowered oxygen is a useful adjunct for ex vivo generation of specific neuron types. Methods and compositions exploiting these findings are described.

11 Claims, 14 Drawing Sheets-

OTHER PUBLICATIONS

Boris Kuzin et al., "Nitric Oxide Regulates Cell Proliferation during Drosophila Development," Cell, vol. 87, Nov. 15, 1996, pp. 639–649.

Thomas G. Storch, "Oxygen Concentration Regulates 5–azacytidine–induced myogenesis in $C_3H/10T1/2$ cultures," Biochimica et Biophysica Acta, 1055, 1990, pp. 126–129.

D.D.W. Cornelison et al., "Single–Cell Analysis of Regulatory Gene Expression in Quiescent and Activated Mouse Skeletal Muscle Satellite Cells," Developmental Biology 191, 1997, pp. 270–283.

Colton, Carol A. et al., "Protection from Oxidation Enhances the Survival of Cultured Mesencephalic Neurons," Experimental Neurology, 132, pp. 54–61 (1995).

Nurse, Colin A. et al., "Role of Basic FGF and Oxygen in Control of Proliferation, Survival, and Neuronal Differentiation in Carotid Body Chromaffin Cells," Developmental Biology, 184, pp. 197–206 (1997).

Czyzyk–Krzeska, Maria F. et al., "Hypoxia Increases Rate of Transcription and Stability of Tyrosine Hydroxylase mRNA in Pheochromocytoma (PC12) Cells," The Journal of Biological Chemistry, vol. 269, No. 1, pp. 760–764, Jan. 7, 1994.

Brewer, G.J. et al., "Survival and Growth of Hippocampal Neurons in Defined Medium at Low Density Advantages of a Sandwich Culture Technique or Low Oxygen," Brain Research (Abstract).

Koller, Manfred R. et al., "Effects of Synergistic Cytokine Combinations, Low Oxygen, and Irradiated Stroma on the Expansion of Human Cord Blood Progenitors," Blood, vol. 80, No. 2, pp. 402–411, Jul. 15, 1992.

Potocnik, Alexandre J., "In vitro generation of lymphoid precursors from embryonic stem cells," The EMBO Journal, vol. 13, No. 22, pp. 5274–5283, 1994.

Kagamu, Hiroshi et al., "Low Oxygen Enhances Endothelin–1 (ET–1) Production and Responsiveness to ET–1 in Cultured Cardiac Myocytes," Biochemical and Biophysical Research Communications, vol. 202, No. 3, pp. 1612–1618, Aug. 15, 1994.

Alice P. Pentland, M.D. et al., "Modulation of Proliferation in Epidermal Keratinocyte Cultures by Lowered Oxygen Tension," Experimental Cell Research, 145, 1983, pp. 31–43.

Maria G. Cipolleschi et al., "The Role of Hypoxia in the Maintenance of Hematopoietic Stem Cells," Blood, 82(7), 1993, pp. 2031–2037.

Alice P. Pentland, M.D. et al., "Effects fo Gas Tension on Epidermal Keratinocyte DNA Synthesis and Prostaglandin Production," The Journal of Investigative Dermatology, vol. 86, No. 2, Feb. 1986, pp. 177–180.

Takashi Horikoshi, M.D. et al., "Effect of Oxygen on the Growth of Human Epidermal Keratinocytes," The Journal of Investigative Dermatology, vol. 86, No. 4, Apr. 1986, pp. 424–427.

Hiromi Takahashi et al., "Effect of Chronic Hypoxia on Skeletal Muscle Fiber Type in Adult Male Rats," Ann. Physiol. Anthrop., 11(6), 1992, pp. 625–630.

Studer, Lorenz et al., "Transplantation of expanded mesencephalic precursors leads to recovery in parkinsonian rats," Nature Neuroscience, Vo. 1, No. 4, pp. 290–295, Aug. 1998.

Genbacev, Olga et al., "Regulation of Human Placental Development by Oxygen Tension," Science, vol. 277, pp. 1669–1672, Sep. 12, 1997.

Iyer, Narayan V. et al., "Cellular and Development Control of $O_2$ homeostasis by hypoxia–inducible factor $1\alpha$," Genes and Development, vol. 12, pp. 149–162, 1998.

Sorokan, Todd et al., "Effect of Hypoxia on Neuronal Production From Embryonic Murine CNS Stem Cells," Molecular Biology of the Cell, vol. 7, pp. 317A, 1996 (Abstract).

Fraser, Scott et al., "Migrating neural crest cells in the trunk of the avian embryo are multipotent", Development, vol. 112, 1991, pp. 913–920.

Maria F. Czyzyk–Krzeska et al., "Regulation of Tyrosine Hydroxylase Gene Expression in the Rat Carotoid Body by Hypoxia," Journal of Neurochemistry, vol. 58, No. 4, 1992, pp. 1538–1546.

Stemple, Derek L. et al., "Isolation of a Stem Cell for Neurons and Glia from the Mammaliam Neural Crest", Cell, vol. 71, 1992, pp 973–985.

Andersen, David J. et al., "Molecular Control of Cell Fate in the Neural Crest: The Sympathoadrenal Lineage", Annu. Rev. Neurosci, Vol. 16, 1993. pp 129–158.

Birren. Susan J., "Sympathetic nueroblasts undergo a development switch in trophic dependence", Development, vol. 119, 1993, pp 597–610.

Verdi, Joseph M. et al., "Neurotrophins Regulate Sequential Changes in Neurotrophin Receptor Expression by Sympathetic Neuroblasts", Neuron, vol. 13, 1994, pp 1359–1372.

Doupe, Allison J. et al., "Environmental Influences in the Development of Neural Crest Derivatives: Glucocorticoids, Growth Factors, and Chromaffin Cell Plasticity", The Journal of Neuroscience, vol. 5, No. 8, 1985, pp 2119–2142.

Varley, Joel E. et al., "Number of Adrenergic and Islet–1 Immunoreactive Cells Is Increased in Avian Trunk Neural Crest Cultures in the Presence of Human Recombinant Osteogenic Protein–1", Developmental Dynamics, vol. 203, 1995, pp 434–447.

Doupe, Allison J. et al., "Small Intensely Fluorescent Cells in Culture: Role of Glucocorticoids, and Growth Factors in Their Development and Interconversions with other Neural Crest Derivatives", The Journal of Neuroscience, vol. 5, No. 8, 1985, pp 2143–2160.

Shah, Nirao M. et al., "Alternative Neural Crest Cell Fates are Instructively Promoted by TGFβ Superfamily Members", Cell, vol. 85, 1996, pp 331–343.

Reissmann, E. et al., "Involvement of bone morphogenetic protein–4 and bone morphogenetic protein–7 in the differentiation of the adrenergic phenotype in developing sympathetic neurons", Development, vol. 122, 1996, pp 2079–2088.

Varley, Joel, E. et al., "BMP–2 and BMP–4, but Not BMP–6, Increase the Number of Adrenergic Cells Which Develop in Quail Trunk Neutral Crest Culture", Experimental Neurology, vol. 140, 1996, pp 84–94.

Gage, Fred H. "CNS Grafting: Potential Mechanisms of Action", Neural Regeneration and Transplantation, 1989, pp 211–226.

Freed, Curt R. et al., "Survival of Implanted Fetal Dopamine Cells and Neurologic Improvement 12 to 46 Months after Transplantation for Parkinson's Disease", The New England Journal of Medicine, vol. 327, No. 22, 1992, pp 1549–1555.

Date, Isao, "Parkinson's Disease, Trophic Factors, and Adrenal Medullary Chromaffin Cell Grafting: Basic and Clinical Studies", Brain Research Bulletin, vol. 40, No. 1, 1996, pp 1–19.

Haavik, Jan et al., "Tyrosine Hydroxlase and Parkinson's Disease", *Molecular Neurobiology,* vol. 16, 1998, pp 285–309.

Morrison, Sean, J. et al., "Prospective Identification, Isolation by Flow Cytometry, and In Vivo Self–Renewal of Multipotent Mammalian Neural Crest Stem Cells", *Cell,* vol. 96, 1999, pp 737–749.

Zawada, W. Michael et al., "Somatic cell cloned transgenic bovine neurons for transplantation in parkinsonian rats", *Nature Medicine,* vol. 4, No. 5, 1998, pp 569–574.

Luquin, M. Rosario et al. "Recovery of Chronic Parkinsonian Monkeys by Autotransplants of Carotid Body Cell Aggregates into Putamen", *Neuron,* vol. 22, 1999, pp 743–750.

Lo, Liching et al., "Specification of Neurotransmitter Identity by Phox2 Proteins in Neural Crest Stem Cells", *Neuron,* vol. 22, 1999, pp 693–705.

Yamamori Tetsuo, et al. "The Cholinergic Neuronal Differentiation Factor from Heart Cells is Identical to Leukemia Inhibitory Factor", *Science,* vol. 246, 1989, pp 1412–1416.

Blancher, Christine et al., "The molecular basis of the hypoxia response pathway: Tumor hypoxia as a therapy target", *Cancer and Metastasis Reviews,* vol. 17, 1998, pp 187–194.

Fraser, Scott et al., "Migrating neural crest cells in the trunk of the avian embryo are multipotent", Development, vol. 112, 1991, pp. 913–920.

Maria F. Czyzyk–Krzeska et al., "Regulation of Tyrosine Hydroxylase Gene Expression in the Rat Carotoid Body by Hypoxia," *Journal of Neurochemistry*, vol. 58, No. 4, 1992, pp. 1538–1546.

Stemple, Derek L. et al., "Isolation of a Stem Cell for Neurons and Glia from the Mammaliam Neural Crest", vol. 71, 1992, pp. 973–985.

Andersen, David J. et al., "Molecular Control of Cell Fate in the Neural Crest: The Sympathoadrenal Lineage", *Annu. Rev. Neurosci*, vol. 16, 1993. pp. 129–158.

Birren. Susan J., "Sympathetic nueroblasts undergo a developmental switch in trophic dependence", *Development*, vol. 119, 1993, pp. 597–610.

Verdi, Joseph M. et al., "Neurotrophins Regulate Sequential Changes in Neurotrophin Receptor Expression by Sympathetic Neuroblasts", *Neuron*, vol. 13, 1994, pp. 1359–1372.

Doupe, Allison J. et al., "Environmental Influences in the Development of Neural Crest Derivatives: Glucocorticoids, Growth Factors, and Chromaffin Cell Plasticity", *The Journal of Neuroscience*, vol. 5, No. 8, 1985, pp. 2119–2142.

Varley, Joel E. et al., "Number of Adrenergic and Islet–1 Immunoreactive Cells Is Increased in Avian Trunk Neural Crest Cultures in the Presence of Human Recombinant Osteogenic Protein–1", *Developmental Dynamics*, vol. 203, 1995, pp. 434–447.

Doupe, Allison J. et al., "Small Intensely Fluorescent Cells in Culture: Role of Glucocorticoids, and Growth Factors in Their Development and Interconversions with other Neural Crest Derivatives", *The Journal of Neuroscience*, vol. 5, No. 8, 1985, pp. 2143–2160.

Shah, Nirao M. et al., "Alternative Neural Crest Cell Fates are Instructively Promoted by TGFβ Superfamily Members", *Cell*, vol. 85, 1996, pp. 331–343.

Reissmann, E. et al. "Involvement of bone morphogenetic protein–4 and bone morphogenetic protein–7 in the differentiation of the adrenergic phenotype in developing sympathetic neurons", *Development*, vol. 122, 1996, pp. 2079–2088.

Varley, Joel, E. et al., "BMP–2 and BMP–4, but Not BMP–6, Increase the Numbers of Adrenergic Cells Which Develop in Quail Trunk Neutral Crest Cultures", *Experimental Neurology*, vol. 140, 1996, pp. 84–94.

Gage, Fred H. "CNS Grafting: Potential Mechanisms of Action", *Neural Regeneration and Transplantation*, 1989, pp. 211–226.

Freed, Curt R. et al., "Survival of Implanted Fetal Dopamine Cells and Neurologic Improvement 12 to 46 months after Transplantation of Parkinson's Disease", *The New England Journal of Medicine*, vol. 327, No. 22, 1992, pp. 1549–1555.

Date, Isao, "Parkinson's Disease, Trophic Factors, and Adrenal Medullary Chromaffin Cell Grafting: Basic and Clinical Studies", *Brain Research Bulletin*, vol. 40, No. 1, 1996, pp. 1–19.

Haavik, Jan et al., "Tyrosine Hydroxlase and Parkinson's Disease", *Molecular Neurobiology*, vol. 16, 1998, pp. 285–309.

Morrison, Sean, J. et al. "Prospective Identification, Isolation by Flow Cytometry, and In Vivo Self–Renewal of Multipotent Mammalian Neural Crest Stem Cells", *Cell*, vol. 96, 1999, pp. 737–749.

Zawada, W. Michael et al., "Somatic cell cloned transgenic bovine neurons for transplantation in parkinsonian rates", *Nature Medicine*, vol. 4, No., 5, 1998, pp. 569–574.

Luquin, M. Rosario et al. "Recovery of Chronic Parkinsonian Monkeys by Autotransplants of Carotid Body Cell Aggregates into Putamen", *Neuron*, vol. 22, 1999, pp. 743–750.

Lo, Liching et al., "Specification of Neurotransmitter Identity by Phox2 Proteins in Neural Crest Stem Cells", *Neuron*, vol. 22, 1999, pp. 693–705.

Yamamori Tetsuo, et al. "The Cholinergic Neuronal Differentiation Factor from Heart Cells Is Identical to Leukemia Inhibitory Factor", *Science*, vol. 246, 1989, pp. 1412–1416.

Blancher, Christine et al., "The molecular basis of the hypoxia response pathway: Tumor hypoxia as a therapy target", *Cancer and Metastasis Reviews*, vol. 17, 1998, pp. 187–194.

* cited by examiner

LOW OXYGEN CULTURING OF CENTRAL NERVOUS SYSTEM PROGENITOR CELLS

RELATED APPLICATIONS

The present application is a continuation-in-part of U.S. application Ser. No. 09/195,569 filed Nov. 18, 1998, U.S. Pat. No. 6,184,035. The entire text of the above referenced application is incorporated herein by reference without prejudice or disclaimer.

FEDERALLY SPONSORED RESEARCH OR DEVELOPMENT

The U.S. Government may have rights in the present invention pursuant to the terms of grant numbers AR40780-8 and AR42671-05 awarded by the National Institutes of Health and DARPA/AFOSR grant number F49620-98-1-0487.

FIELD OF THE INVENTION

The present invention relates to the growth of cells in culture. More particularly, the present invention provides methods and compositions for increasing cell survival, cell proliferation and/or cell differentiation along specific pathways by growing the cells in low ambient oxygen conditions.

BACKGROUND OF THE INVENTION

In a time of critical shortages of donor organs, efforts to bring cellular transplantation into the clinical arena are urgently needed (Neelakanta & Csete, 1996). Indeed, cellular and tissue transplantation is now well recognized as a desirable technique for the therapeutic intervention of a variety of disorders including cystic fibrosis (lungs), kidney failure, degenerative heart diseases and neurodegenerative disease. However, although this may be a desirable and much needed intervention, a major impediment to this type of therapeutic intervention is the lack of an available supply of viable, differentiated cells. Generally differentiated cells cannot be readily expanded in culture. Thus, methods of increasing the number and/or availability of differentiated, viable cells are needed.

The central nervous system (CNS) (brain and spinal cord) has poor regenerative capacity which is exemplified in a number of neurodegenerative disorders, such as Parkinson's Disease. Although such diseases can be somewhat controlled using pharmacological intervention (L-dopa in the case of Parkinson's Disease), the neuropathological damage and the debilitating progression is not reversed. Cell transplantation offers a potential alternative for reversing neuropathological damage as opposed to merely treating the consequences of such damage.

Cultured CNS stem cells can self-renew, and after mitogen withdrawal, have an intrinsic capacity to generate oligodendrocytes, astrocytes, and neurons in predictable proportions (Johe et al., 1996). Manipulation of this intrinsic differentiation capacity in culture has been used to define a complex array of factors that maintain, amplify, or diminish a particular differentiated phenotype. Most such studies emphasize a primary role for transcription factors in defining CNS lineage identity, as well as growth and trophic factors acting locally and over long distances (Johe et al., 1996, Panchinsion et al., 1998). Dopaminergic neurons and their progenitors from these cultures are of special interest as potential sources of replacement cellular therapies for Parkinson's Disease patients (reviewed in Olanow et al., 1996).

Ideally, ex vivo culture conditions should reproduce the in vivo cellular environment with perfect fidelity. This ideal is especially pertinent when explants are used to study development, because conditions may be defined for cell fate choice and differentiation. For CNS stem cell cultures, in particular, maximizing survival, proliferation, and cell fate choice leading to dopaminergic neurons is essential for future cellular transplant therapies. Thus, understanding and control of the differentiation of such cells is crucial for providing a viable, useful product that can be used in transplantation or for studying the behavior of CNS cells, in vitro, in response to various conditions.

In embryogenesis, each tissue and organ develops by an exquisitely organized progression in which relatively unspecialized or "undifferentiated" progenitor or stem cells give rise to progeny that ultimately assume distinctive, differentiated identities and functions. Mature tissues and organs are composed of many types of differentiated cells, with each cell type expressing a particular subset of genes that in turn specifies that cell's distinctive structure, specialized function, and capacity to interact with and respond to environmental signals and nutrients. These molecular, structural and functional capacities and properties comprise the cell phenotype. Similarly, coupled cell proliferation and/or differentiation occurs, in the presence of changing local $O_2$ supply, when an injured or degenerating adult tissue undergoes repair and regeneration. The level of oxygen is especially pertinent in many regeneration paradigms in which normal blood supply is reduced or even transiently stopped by trauma or embolic events (myocardial infarction, stroke and the like).

Therefore, in clinical settings, gases are appreciated as a primary variable in organ survival, with oxygen as the critical gas parameter. Virtually all modern cell culture is conducted at 37° C. in a gas atmosphere of 5% $CO_2$ and 95% air. These conditions match core human body temperature and approximate quite well physiologic $CO_2$ concentrations. For example, mean brain tissue $CO_2$ is 60 mm Hg or about 7% (Hoffman et al., 1998). However, in striking contrast, oxygen in standard tissue culture does not reflect physiologic tissue levels and is, in fact, distinctly hyperoxic.

At sea level, (unhumidified) room air contains 21% $O_2$ which translates into an oxygen partial pressure of 160 mm Hg [0.21(760 mm Hg)]. However, the body mean tissue oxygen levels are much lower than this level. Alveolar air contains 14% oxygen, arterial oxygen concentration is 12%, venous oxygen levels are 5.3%, and mean tissue intracellular oxygen concentration is only 3% (Guyton, and Hall, 1996). Furthermore, direct microelectrode measurements of tissue $O_2$ reveal that parts of the brain normally experience $O_2$ levels considerably lower than total body mean tissue oxygen levels, reflecting the high oxygen utilization in brain. These studies also highlight considerable regional variation in average brain oxygen levels (Table 1) that have been attributed to local differences in capillary density. Mean brain tissue oxygen concentration in adult rates is 1.5% (Silver and Erecinska, 1988), and mean fetal sheep brain oxygen tension has also been estimated at 1.6% (Koos and Power, 1987).

TABLE 1

Regional rat brain tissue partial pressures of oxygen measured by microelectrode

| Brain area | % O$_2$ |
| --- | --- |
| Cortex (gray) | 2.5–5.3 |
| Cortex (white) | 0.8–2.1 |
| Hypothalamus | 1.4–2.1 |
| Hippocampus | 2.6–3.9 |
| Pons, fornix | 0.1–0.4 |

Adapted from Silver, L, Erecinska, M. Oxygen and ion concentrations in normoxic and hypoxic brain cells. In *Oxygen Transport to Tissue XX*, 7–15, edited by Hudetz and Bruley, Plenum Press, New York (1988).

Thus, from the discussion above it is clear that under standard culture conditions, the ambient oxygen levels are distinctly hyperoxic, and not at all within physiologic ranges. These conditions of cell growth are have been historically inadequate for generating cells and tissues for transplantation into the brain or other area of the body or for providing an accurate in vitro model of what is occurring in vivo. Thus, there remains a need for methods to produce differentiated cells which can be used for therapeutic and research purposes. The present invention is directed to providing such methods.

BRIEF SUMMARY OF THE INVENTION

The present invention is directed to growing cells in low ambient oxygen conditions in order to mimic the physiological oxygen conditions with greater fidelity. The growth of these cells in such conditions provides certain surprising and unexpected results. These results are exploited and described in further detail herein. More particularly, the present invention describes methods that may independently be useful in increasing cell survival, cell proliferation and/or cell differentiation along specific pathways.

In specific embodiments, the present invention describes a method of increasing cell differentiation comprising culturing undifferentiated central nervous system (CNS) cells in low ambient oxygen conditions, wherein the low ambient oxygen conditions promotes the cellular differentiation of the neuronal cells. The definitions of low ambient oxygen conditions are described in depth elsewhere in the specification. However, it is contemplated that in specific embodiments the low ambient oxygen conditions comprise an ambient oxygen condition of between about 0.25% to about 18% oxygen. In other embodiments, the ambient oxygen conditions comprise an ambient oxygen condition of between about 0.5% to about 15% oxygen. In still other embodiments, the low ambient oxygen conditions comprise an ambient oxygen condition of between about 1% to about 10% oxygen. In further embodiments, the low ambient oxygen conditions comprise an ambient oxygen condition of between about 1.5% to about 6% oxygen. Of course, these are exemplary ranges of ambient oxygen conditions to be used in culture and it should be understood that those of skill in the art will be able to employ oxygen conditions falling in any of these ranges generally or an oxygen conditions between any of these ranges that mimics physiological oxygen conditions for CNS cells. Thus, one of skill in the art could set the oxygen culture conditions at 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%. 11%, 11.5%, 12%, 12.5%, 13%, 13.5%, 14%, 14.5%, 15%, 15.5%, 16%, 16.5%, 17%, 17.5%, 18%, 18.5%, or any other oxygen condition between any of these figures.

The cells employed in the method described may be any cells that are routinely used for CNS studies. As such, the cells may be primary tissue culture cells or derived from a cell line. The cells may be fetal cells or adult cells. In specific embodiments, it is contemplated that the cells may be selected from the group consisting of central nervous system stem cells, spinal cord-derived progenitor cells, glial cells, astrocytes, neuronal stem cells, central nervous system neural crest-derived cells, neuronal precursor cells, neuronal cells, hepatocytes, and bone marrow derived cells. In preferred embodiments, it is contemplated that the cells may be mecencephalic progenitor cells, lateral ganglion precursor cells, cortical precursor cells, astrocytes or neuroblasts.

The method may comprise determining the amount, level or degree of differentiation. Those of skill in the art are familiar with technologies employed to determine cellular differentiation. The differentiation may determined by monitoring a differentiation specific phenotype in the cells. For example, the differentiation specific phenotype determined may be by monitoring message level, protein level, subcellular localization, functional assays or morphological changes.

There are various techniques that may be employed for determining message level including but not limited to PCR™, in situ hybridization, RNAse protection assay, or single cell PCR™. In specific embodiments, the present invention may monitor the message level for nestin, tyrosine hydroxylase, GAPDH; BDNF; GDNF; FGFR3; En1; FGF8; SHH; Ptx3; Nurr1; VEGF; EPO; HIF1α or VHL. Of course these are exemplary differentiation markers for CNS cells or markers of cellular responses to oxygen and it is contemplated that those of skill in the art will be able to substitute additional similar markers for the markers specifically described herein without undue experimentation. Other embodiments monitor protein level by, for example, using antibody staining, HPLC, western blotting or immunoprecipitation. In more particular embodiments, the protein level monitored is the level of nestin, tyrosine hydroxylase, dopamine β-hydroxylase or dopamine transporter. The functional assay typically will be one that monitors a particular function of the selected CNS cells. A particularly useful functional assay may be one which monitors the rate of dopamine production.

A preferred feature of the present invention is that the low oxygen conditions produce a cell population that is enriched in dopaminergic neurons as compared to a similar cell population that is grown in 20% oxygen incubator conditions. Another preferred embodiment is that the low oxygen conditions produce a cell population that is enriched in serotoninergic neurons as compared to a similar cell population that is grown in 20% oxygen incubator conditions. In still additional embodiments, the low oxygen conditions produce a cell population that is depleted in GABAnergic neurons as compared to a similar cell population that is grown in 20% oxygen incubator conditions. Further, certain methods of the present invention will provide low oxygen conditions to produce a cell population that is depleted in glutaminergic neurons as compared to a similar cell population that is grown in 20% oxygen incubator conditions.

In preferred embodiments, the method may further comprise growing the cells in the presence of a neuronal growth stimulant, mitogen, cytokine, neuroprotective factor or an anti-apoptotic agent. The inventors have found that there was a significant increase in EPO expression as a result of lowered oxygen versus 20% $O_2$. In particular embodiments, the differentiated phenotype is retained after transfer of the cells from the low ambient oxygen conditions to 20% oxygen culture conditions. In specific embodiments, it is contemplated that the cells may be grown in low ambient oxygen conditions for multiple generations prior to transfer to 20% oxygen culture conditions. In other embodiments, the cells may be continuously maintained in low ambient oxygen conditions.

Another aspect of the present invention provides a method of inhibiting apoptosis of a CNS cell in culture comprising growing the cell in low ambient oxygen conditions.

Yet another embodiment provides a method of increasing the expansion of a CNS cell in culture comprising growing the cell in low ambient oxygen, wherein the cells exhibit increased expansion in the low ambient oxygen as compared to growing the cell in 20% oxygen incubator conditions.

In an additional embodiment, the present invention further contemplates a method of increasing cell proliferation in culture comprising growing CNS cells in low ambient oxygen, wherein the growth in low ambient oxygen increases cell proliferation compared to growing the cells in 20% oxygen incubator conditions.

Also provided is a method of preparing a cell for use against a neurodegenerative disorder comprising obtaining a population of CNS cells and growing the cells in low ambient oxygen conditions wherein the low ambient oxygen conditions increases the expression of a gene involved in the neurodegenerative disease. In specific embodiments, the neurodegenerative disease is Parkinson's Disease and the gene is tyrosine hydroxylase (TH).

The method further may comprise contacting the cell(s) with a first polynucleotide encoding a dopamine biosynthetic protein under conditions suitable for the expression of the protein wherein the polynucleotide is under the transcriptional control of a promoter active in the cells. In addition, the method further may comprise contacting the cell with a first polynucleotide encoding a dopamine releasing protein under conditions suitable for the expression of the protein wherein the polynucleotide is under the transcriptional control of a promoter active in the cells. Also contemplated is a method further comprising contacting the cell with a second polynucleotide encoding a dopamine releasing protein under conditions suitable for the expression of the protein wherein the polynucleotide is under the transcriptional control of a promoter active in the cells. Other embodiments involve contacting the cell with a second polynucleotide encoding a dopamine biosynthetic protein under conditions suitable for the expression of the protein wherein the polynucleotide is under the transcriptional control of a promoter active in the cells.

In more particular embodiments, the dopamine biosynthesis protein may be TH; L-amino acid decarboxylase (AADC), erythropoietin or any other protein directly or indirectly involved in dopamine synthesis. The dopamine releasing protein is a vesicular monoamine transporter (VMAT), which may be VMAT1 or VMAT2. In specific embodiments, the first and second polynucleotides are under control of different promoters. The promoter may be any promoter known to those of skill in the art that will be operative in the cells being used. For example, it is contemplated that the promoter may be CMV IE, SV40 IE, β-actin, TH promoter, AADC promoter, and nestin promoter. It is contemplated that the first and second polynucleotides each may be covalently linked to a polyadenylation signal.

Also encompassed by the present invention is a cell produced according to the method comprising obtaining a starting CNS cell and growing the cell in low ambient oxygen conditions wherein the conditions produce a differentiated neuronal cell. In specific embodiments, the starting cell is a nestin-positive cell. More particularly, the low ambient conditions produce a nestin-negative differentiated cell more rapidly and in greater numbers than traditional cell culture conditions. In specific embodiments, the low ambient conditions produce a TH positive cell. In other embodiments, the cell further comprises an expression vector comprising a polynucleotide encoding an exogenous gene wherein the polynucleotide is operatively linked to a promoter.

Another aspect of the present invention provides a method of treating Parkinson's disease in a subject comprised of obtaining cells suitable for transplanting in the subject; growing the cells in low ambient oxygen conditions; and implanting the cells grown in the low ambient oxygen conditions into the subject; wherein the implanted cells have an increased capacity to produce dopamine in the subject as compared to similar cells grown in 20% oxygen incubator conditions. In specific embodiments, the cells are from the subject and have been transduced with a polynucleotide that expresses a protein that increases dopamine production and are treated or expanded in lowered oxygen conditions. In other preferred embodiments, the cells are CNS cells from a source other than the subject. In preferred embodiments, the cells are transduced with a polynucleotide that expresses a protein that increases dopamine production and are treated or expanded in lowered oxygen conditions.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3. CNS precursors cultured in lowered (vs. 20%) $O_2$ have reduced rates of apoptosis.

FIG. 5. Lowered $O_2$ culturing improves the yield of functional precursor-derived dopaminergic neurons. FIG. 5D-2 shows typical chromatogram for dopamine detection in lowered and 20% $O_2$ cultures.

FIG. 7. Differential gene expression in mesencephalic precursors at lowered and 20% $O_2$ assessed by RT-PCR.

DETAILED DESCRIPTION OF THE INVENTION

Figure 1:
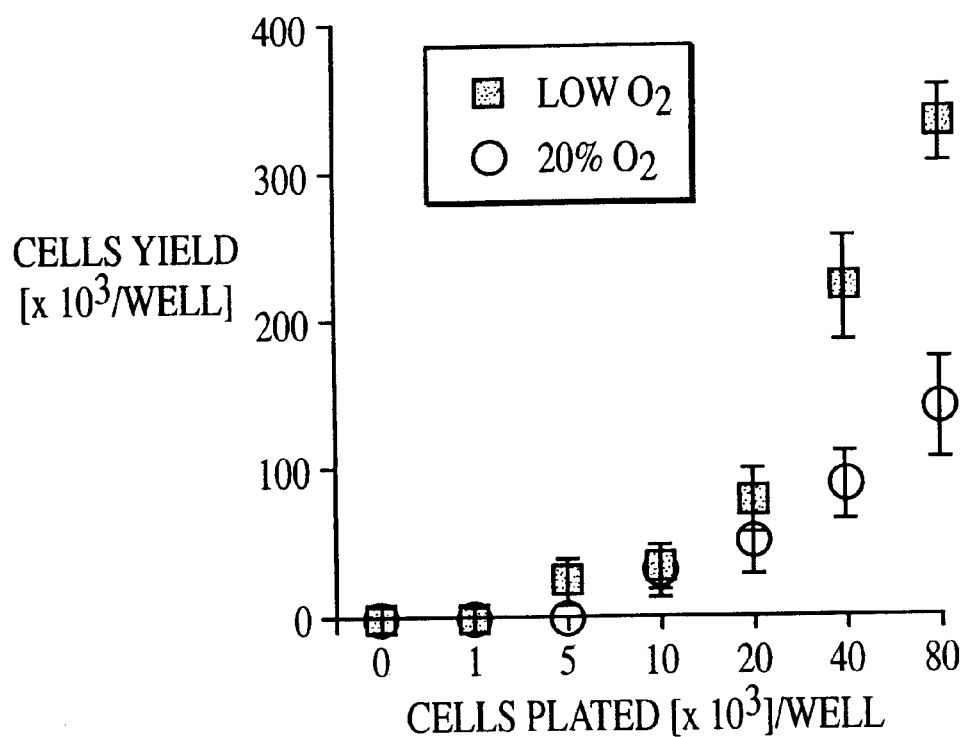
FIG. 1. Effect of lowered oxygen on precursor yield in vitro at varying plating densities. Striatal cultures were expanded with bFGF in lowered or ambient oxygen, and total cell numbers assessed after 5 days of proliferation when over 95% of cells are nestin+ precursors. Significantly increased cell numbers were detected at all densities in lowered $O_2$ compared to 20% oxygen.

In order for cell transplantation therapies to become widely and universally used there is a need for availability of appropriately differentiated, viable cells. Preferably, these cells need to be resilient enough that they can be cryopreserved without loss of phenotypic integrity. The high incubator $O_2$ levels in which the cells are grown at ambient air $O_2$ levels (referred to herein as traditional $O_2$ conditions; or 20% $O_2$ culture conditions) do not facilitate the production of such cells. These cells often do not survive, proliferate or differentiate in sufficient numbers to be useful. As such expansion of these cells in traditional culture yields a cell that is at best inadequate for use in in vitro model assay studies let alone for use in transplantation.

The present invention is directed towards providing methods and compositions for producing cells that are differentiated, viable, amenable to cryopreservation and provide an accurate indication of how such cells behave biochemically in an in vivo setting. As such, these methods will provide cells that can be used in vitro to perform characterization studies or in vivo as replacement therapies for cells that have been damaged by disease, injury resulting from trauma, ischemia, or a drug-induced injury. Further, it should be noted that the method leads to increased survival of undifferentiated precursors that could also be used for transplantation, which when placed in the appropriate environmental conditions will differentiate down the appropriate pathway.

The present invention particularly contemplates the use of culture conditions using subatmospheric/physiological oxygen to culture or enrich a population of neuronal cells with cells that are expanded and/or differentiated to express a particular neuronal phenotype. The increase in cell differentiation may be such that the process of a cell being converted from a primitive undifferentiated state to one in which a particular cellular phenotype (dopaminergic phenotype; GABAergic phenotype; serotoninergic phenotype or the like) is expressed. Specifically, it appears that growth in low $O_2$ conditions results in an enrichment in dopaminergic and serotinergic neuronal populations, whereas GABAergic and glutaminergic neurons are relatively decreased. These enriched populations may be subject to further enrichment through such methods such as cell sorting.

Alternatively, it may be that the increase in differentiation produced by this method is such that the relative percentage of cells that go on to differentiate (as opposed to remaining in an undifferentiated state) is increased in low oxygen. However, incubation of a pluripotent cell line under low $O_2$ incubation conditions in vitro, will allow the manipulation or skewing of the direction of differentiation of the cell population. Thus, the oxygen is used to control the number and percentage of one type of cell in the population increased or decreased because the differentiation pathway changes under influence of the gas. Thus, enrichment of the CNS cells by physiologic or low levels of oxygen may be the result of one or more mechanisms that include (1) increase in the absolute number of CNS cells, (2) enrichment by selective survival of CNS cells, (3) enrichment of CNS by their selective proliferation or (4) enrichment of specific differentiation pathways.

Any increase in the number of CNS cells is significant in that more cells are then available to regenerate a greater volume of new tissue. An enrichment, even without increase in number, is important in applications where limitations on total cell number are pertinent or when the effects of the non-CNS progenitor cell contaminants are negative for the desired outcome or for defining the material adequately. Any enhancement of survival of the CNS cell, even without increase in cell number or any enrichment of cell types is valuable in settings where culture is required (i.e., to handle tissue before administration of cell therapy, or to permit any other procedure during which the cells must survive such as transfection of genes, drug treatment, or enrichment by cell sorting or other additional procedures).

A particular embodiment of the present invention demonstrates that growth of CNS cells, or indeed any pluripotent stem cell in subatmospheric culture conditions reduces the level of apoptotic and non-apoptotic cell death. It is likely that the increased survival of the cells may be due to both an inhibition of apoptosis and non-apoptotic death. Apoptosis or programmed cell death is a well known phenomenon and can be measured by techniques well know to those of skill in the art.

A particular and novel aspect of the methods of the present invention is that such methods all employ low ambient culture growth conditions. By the term "low ambient oxygen conditions", the present invention refers to any culturing conditions below atmospheric oxygen. Thus in particular embodiments, low ambient $O_2$ conditions are defined as between about 0.5% and about 18%. Ideally, the culture oxygen conditions are kept as close as possible to the normal physiological oxygen conditions in which a particular cell would be found in in vivo the better. Clearly, this will mean that those conditions employed for cells will depend on the regional origin of a particular cell. For example, cells from an alveolar origin may prefer growth at about 14% $O_2$; cells from an arterial source will prefer an oxygen concentration of about 12%; whereas those from certain regions of the brain may prefer oxygen conditions as low as about 1.5%.

It should be noted that the low ambient oxygen conditions are not to be considered the same as "hypoxic" conditions. The low ambient oxygen conditions are intended to mimic physiological conditions. As defined herein "hypoxic conditions" are those in which the oxygen level is less than 0.1% $O_2$ (Gross et al., 1999).

The low ambient oxygen conditions thus will be used to promote differentiation of CNS cells, inhibit apoptosis of cells in culture, increase expansion of cells, and otherwise make such cells amenable for use in transplantation. Such methods and compositions are outlined in further detail below.

Definitions

The present section provides definitions of the terms used in the present invention in order to facilitate a better understanding of the invention.

A "stem cell" is a relatively undifferentiated cell that can be induced to proliferate and that can produce progeny that subsequently differentiate into one or more mature cell types, while also retaining one or more cells with parental developmental potential. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype.

"Progenitor cells" have a cellular phenotype that is more primitive (i.e., is at an earlier step along a developmental pathway or progression than is a fully differentiated cell). Often, progenitor cells also have significant or very high proliferative potential. Progenitor cells may give rise to multiple distinct differentiated cell types or to a single differentiated cell type, depending on the developmental pathway and on the environment in which the cells develop and differentiate. Like stem cells, it is possible that cells that begin as progenitor cells might proceed toward a differentiated phenotype, but then "reverse" and re-express the progenitor cell phenotype.

"Differentiation" refers to the developmental process whereby cells assume a specialized phenotype, i.e., acquire one or more characteristics or functions distinct from other cell types. In most uses, the differentiated phenotype refers to a cell phenotype that is at the mature endpoint in some developmental pathway. In many but not all tissues, the process of differentiation is coupled with exit from the cell cycle—in these cases, the cells lose or greatly restrict their capacity to proliferate when they differentiate.

"Subatmospheric" conditions mean any oxygen concentration below about 20%, preferably below about 15%, more preferably below about 10%, at sea level. The term subatmoshpheric may be used herein interchangeably with "low oxygen conditions" defined above.

"Atmospheric $O_2$ conditions" are those conditions found in the air, i.e., 20–21% $O_2$. As used herein this term is used interchangeably with the term "traditional" $O_2$ conditions as traditional tissue culture incubators are kept at atmospheric $O_2$ conditions.

"Physiologic" oxygen levels are the range of oxygen levels normally found in healthy tissues and organs. These levels vary depending on tissue type (Table 1). However, it is of note that this rate is below 15% in all tissues and below 8% in most tissues. Thus the physiological oxygen levels can range from about 15% to about 1.5% depending upon the region of the body being measured.

"Hypoxia" occurs when the normal physiologic levels of oxygen are not supplied to a cell or tissue. "Normoxia" refers to normal physiologic levels of oxygen for the particular cell type, cell state or tissue in question. "Anoxia" is the absence of oxygen. "Hypoxic conditions" are those leading to cellular hypoxia. These conditions depend on cell type, and on the specific architecture or position of a cell within a tissue or organ, as well as the metabolic status of the cell. A critical point is that in most cell biology research of the past 25 years, ambient atmospheric oxygen levels of 20–21% are routinely called and experimentally taken to be "normoxic," but this assumption is physiologically erroneous. In this historic context, much cell culture literature refers to any condition with oxygen lower than ambient atmospheric as "hypoxic," but this usage is also physiologically incorrect.

"Acidosis" means that the pH is below normal physiologic levels.

"Enriching" of cells means that the yield (fraction) of cells of one type is increased over the fraction of cells in the starting culture or preparation.

"Proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

"Regeneration" means re-growth of a cell population, organ or tissue after disease or trauma.

Other terms used throughout the specification will have the meaning commonly assigned by those of skill in the art unless otherwise stated.

Central Nervous System Cells

As mentioned earlier, a particular advantage of the present invention is that it can be used to generate viable cells or tissue that can be used to ameliorate neurodegenerative disorders. Such cells or tissue upon transplantation can be referred to as a graft. The cells for transplantation can include but are not limited human or animal neurons for stroke, brain and spinal cord injury, Alzheimer's Disease, Huntington's Disease and other neurodegenerative disorders; septal and GABAergic cells for epilepsy; ventral mesencephalic or other CNS dopaminergic cells for treatment of Parkinson's Disease; and trophic factor secreting cells for neurological disorders, or even certain psychiatric disorders. The cells to be used as grafts can be from primary tissue or even from certain cell lines. Further it should be understood that any of the cell types mentioned herein throughout may be adult cells or from a fetal origin.

For treatment of neurological disorders, the present invention will produce differentiated neural stem cells that proliferate and differentiate. Undifferentiated neural progenitor cells differentiate into neuroblasts and glioblasts which give rise to neurons and glial cells. During development, cells that are derived from the neural tube give rise to neurons and glia of the CNS. Certain factors present during development, such as nerve growth factor (NGF), promote the growth of neural cells. Methods of isolating and culturing neural stem cells and progenitor cells are well known to those of skill in the art (Hazel and Muller, 1997; U.S. Pat. No. 5,750,376).

Suitable neural cells may be obtained from suitable solid tissues these include any organ or tissue from adult, postnatal, fetal or embryonic mammalian tissue. Any mammal can be used in this invention, including mice, cattle, sheep, goat, pigs, dogs, rats, rabbits, and primates (including human). Specific examples of suitable solid tissues include neurons or central nervous system supporting cells derived from brain tissue, germ cells or embryonic stem cells. Stem cells and progenitor cells isolated from any other solid organ (liver, pancreas, spleen, kidney, thyroid, etc.) or those from marrow, spleen or blood are also amenable candidates for culturing under physiologic or hypoxic conditions.

Hazel and Muller describe methods of isolating, culturing, and differentiating rat brain neuroepithelial stem cells from both fetal and adult rat brains. Briefly, neural precursors are removed from desired regions of the fetal rat central nervous system by dissection, dissociated to a single-cell suspension, and plated on tissue culture dishes in medium containing the mitogen basic fibroblast growth factor (bFGF). Initially, many of the differentiated neurons die. Proliferating cells are then harvested in a buffered solution. The passaged cells are relatively homogenous for multipotent precursors. To induce differentiation to neurons and glia, the media containing bFGF is removed and replaced with media lacking bFGF.

Subatmospheric culturing conditions can be used in such a protocol from the start of stem cell isolation, in order to enrich the stem cell pool and enhance differentiation into a greater number of cells. Subatmospheric/physiologic culture conditions can also be used after initial plating and division, to up-regulate certain gene products in the more differentiated brain cells. Subatmospheric/physiologic culture conditions can also be used throughout the process to enhance the function of the entire population for transplantation.

Detection of neural stem cell derivatives can be determined by antibody staining. For example, central nervous system multipotential stems are marked by high level expression of the intermediate filament, nestin (Hazel & Muller, 1997). The differentiated neurons are marked by the antibody TUJ1 (O'Rourke et al., 1997), oligodendrocytes by GalC (Bosio et al., 1996), and astrocytes by GFAP antibodies (Rutka et al., 1997).

The methods of the present invention may be used to produce neural cells containing a heterologous gene. Methods of producing cells of neural origin comprising a heterologous gene and uses of such cells are described in U.S. Pat. No. 5,750,376 (incorporated herein by reference).

Culture Conditions

Suitable medium and conditions for generating primary cultures are well known in the art and vary depending on cell type. For example, skeletal muscle, bone, neurons, skin, liver, and embryonic stem cells are all grown in media differing in their specific contents. Furthermore, media for one cell type may differ significantly from lab to lab and institution to institution. As a general principle, when the goal of culturing is to keep cells dividing, serum is added to the medium in relatively large quantities (10–20% by volume). Specific purified growth factors or cocktails of multiple growth factors can also be added or sometimes used in lieu of serum. As a general principle, when the goal of culturing is to reinforce differentiation, serum with its mitogens is generally limited (serum about 1–2% by volume).

Specific factors or hormones that promote differentiation and/or promote cell cycle arrest can also be used.

Physiologic oxygen and subatmospheric oxygen conditions can be used at any time during the growth and differentiation of cells in culture, as a critical adjunct to selection of specific cell phenotypes, growth and proliferation of specific cell types, or differentiation of specific cell types. In general, physiologic or low oxygen-level culturing is accompanied by methods that limit acidosis of the cultures, such as addition of strong buffer to medium (such as Hepes), and frequent medium changes and changes in $CO_2$ concentration.

Cells can be exposed to the low oxygen conditions using a variety of means. Specialized laboratory facilities may have completely enclosed environments in which the oxygen levels are controlled throughout a dedicated, isolated room. In such specialized areas, low oxygen levels can be maintained throughout the isolation, growth and differentiation of cells without interruption. Very few laboratories have such specialized areas. Physiologic or low oxygen culturing conditions also can be maintained by using commercially-available chambers which are flushed with a pre-determined gas mixture (e.g., as available from Billups-Rothenberg, San Diego Calif.). As an adjunct, medium can be flushed with the same gas mixture prior to cell feeding. In general, it is not possible to maintain physiologic or low oxygen conditions during cell feeding and passaging using these smaller enclosed units, and so, the time for these manipulations should be minimized as much as possible. Any sealed unit can be used for physiologic oxygen or low oxygen level culturing provided that adequate humidification, temperature, and carbon dioxide are provided.

In addition to oxygen, the other gases for culture typically are about 5% carbon dioxide and the remainder is nitrogen, but optionally may contain varying amounts of nitric oxide (starting as low as 3 ppm), carbon monoxide and other gases, both inert and biologically active. Carbon dioxide concentrations typically range around 5% as noted above, but may vary between 2–10%. Both nitric oxide and carbon monoxide are typically administered in very small amounts (i.e. in the ppm range), determined empirically or from the literature.

The optimal physiologic or low oxygen level conditions for any given cell type or any particular desired outcome will vary. A skilled artisan could determine suitable subatmospheric conditions by generating an oxygen dose response curve, in which carbon dioxide is kept constant, and oxygen levels are varied (with nitrogen as the remaining gas). For example, to determine the optimal ambient oxygen culturing conditions for expansion of a CNS cell, one would establish cultures from an organ system. The initial culture is mixed, consisting of some differentiated cells, cells of other developmental lineages or pathways, as well as CNS cells. After exposure to the various oxygen levels (e.g. 1%, 2%, 5%, 10% and 15%), the number and function of CNS cells is assessed by methods appropriate to the system. In some cases, a constellation of molecular markers is available to rapidly identify the cell population. But in other cases, a single marker coupled with proliferation assays is appropriate, while in other cases proliferation assays alone are appropriate. In some cases all or some of the above assays are coupled with bioassays to follow the differentiation potential of the presumed stem cells. Overall, the precise assays used to determine stem cell and/or progenitor response to oxygen levels are dependent on the nature of the system examined as well as available markers and techniques specific to that system.

The timing of physiologic or low oxygen conditions is also part of the oxygen dose response curve. Some cells may be more or less sensitive to oxygen during isolation or immediately after isolation while some cells may respond only after some time in culture. The timing of physiologic or low oxygen conditions absolutely and in relation to other manipulations of the cultures is part of assessing the optimal oxygen culturing conditions. Furthermore, the mitogenic effects of other gases may be synergistic with physiologic or low oxygen conditions. Different gene regulatory networks may be induced by low/physiologic oxygen culturing during different phases of culture. During expansion of the cells, low oxygen may induce gene expression distinct from that induced by low oxygen during differentiation.

The cells are typically exposed to low oxygen level conditions for a time sufficient to enrich the population of progenitor/stem cells compared to other cell types. Typically this is for 1 or more hours, preferably 3 or more hours, more preferably 6 or more hours, and most preferably 12 or more hours, and may be continuous. The temperature during the culture is typically reflective of core body temperature, or about 37° C., but may vary between about 32° C. and about 40° C. Other important embodiments may simply achieve an increase in cell absolute number or promote the survival of cells.

Following an initial exposure to low or physiologic oxygen culturing conditions, cells can be maintained in these conditions or returned to normal laboratory oxygen conditions, depending on the desired outcome.

It is understood that the initial medium for isolating the CNS cells, the medium for proliferation of these cells, and the medium for differentiation of these cells can be the same or different. All can be used in conjunction with low or physiologic oxygen level culturing. The medium can be supplemented with a variety of growth factors, cytokines, serum, etc. Examples of suitable growth factors are basic fibroblast growth factor (bFGF), vascular endothelial growth factor (VEGF), epidermal growth factor (EGF), transforming growth factors (TGFα and TGFβ), platelet derived growth factors (PDGFs), hepatocyte growth factor (HGF), insulin-like growth factor (IGF), insulin, erythropoietin (EPO), and colony stimulating factor (CSF). Examples of suitable hormone medium additives are estrogen, progesterone, testosterone or glucocorticoids such as dexamethasone. Examples of cytokine medium additives are interferons, interleukins, or tumor necrosis factor-α (TNFα). One skilled in the art will test additives and culture components at varied oxygen levels, as the oxygen level may alter cell response to, active lifetime of additives or other features affecting their bioactivity. In addition, the surface on which the cells are grown can be plated with a variety of substrates that contribute to survival, growth and/or differentiation of the cells. These substrates include but are not limited to laminin, poly-L-lysine, poly-D-lysine, polyornithine and fibronectin.

Additional Factors for Promotion of Growth and Differentiation

As described herein, the present invention provides methods of increasing the survival, differentiation and phenotypic integrity of CNS cells. This method generally involves growing these cells in vitro within physiological oxygen parameters. There is now a wealth of literature pointing to other factors that may increase the survival of such cells. It is contemplated that the use of some of these factors in combination with the growth conditions of the present invention will be useful.

Much of this interest has focused on finding trophic factors. These factors are able to increase the survival of dopaminergic cells prepared for transplantation; maintain the in situ survival post-transplantation of embryonic neurons transplanted into the striatum; as well as increase graft volume, and thereby re-innervate a larger part of the caudate and putamen which has been shown to have effect both in vitro and in vivo.

Trophic factors such as NGF, bFGF, EGF, IGF I and II, TGFβ1-3, PDGF, brain derived growth factor (BDNF), ganglion derived growth factor (GDNF), neurotrophin (NT)-3, NT-4, and ciliary neuronal trophic factor (CNTF), (Engele and Bohn, 1996; Mayer et al., 1993a and 1993b; Knusel et al., 1990, 1991; Poulsen et al., 1994; Nikkhah et al., 1993; Othberg et al., 1995; Hyman et al., 1991) have been investigated and shown to have pronounced effects in vitro.

MPTP and 6-OHDA lesions in primates are models of certain neurodegenerative disorders. It has been shown that the effects of such lesions can be reversed in primates and rats (Gash et al., 1996) by the addition of NGF or bFGF to the cell suspension prior to grafting. The same factors also have been shown to increase graft survival, if added to the cell suspension prior to grafting (Chen el al., 1996; Dunnett and Bjorkland., 1994). Additional studies showed an increased graft survival rate in transplanted neurons derived from a neural progenitor (CINP) cell line, that were retrovirally transduced with NGF (Martinez-Serrano et al., 1995) and astrocytes transduced with BDNF (Yoshimoto et al., 1995). GDNF has been shown to increase graft survival, extend fiber outgrowth and alleviate behavioral effects after 6-hydroxydopamine lesions in the striatum of rats (Sauer et al., 1994; Bowenkamp et al., 1995; Rosenblad et al., 1996; Olson, 1996).

Thus these and other factors that may prolong the survival of the CNS cells either in vitro or in vivo are contemplated for use in the growth and maintenance conditions described in the present invention.

Transplantation Methods

Laboratory and clinical studies have shown the transplantation of cells into the CNS is a potentially significant alternative therapeutic modality for neurodegenerative disorders such as Parkinson's disease (Wictorin et al., 1990; Lindvall et al., 1990; Sanberg et al., 1994; Bjorklund and Stenevi, 1985; Freeman et al., 1994). In some cases, transplanted neural tissue can survive and form connections with the CNS of the recipient, i.e. the host (Wictorin et al., 1990). When successfully accepted by the host, the transplanted cells and/or tissue have been shown to ameliorate the behavioral deficits associated with the disorder (Sanberg et al., 1994). The obligatory step for the success of this kind of treatment is to have enough viable cells available for the transplant. The physiologic/subatmospheric culturing conditions described herein can be used to differentiate specific populations of CNS cells useful for transplantation, and to expand the number of available CNS cells derived from a variety of culture systems.

In addition to cell cultures described above, fetal neural tissue is another important source for neural transplantation (Lindvall et al., 1990; Bjorklund, 1992; Isacson et al., 1986; Sanberg et al., 1994). Other viable graft sources include adrenal cells and various cell types that secrete neural growth factors and trophic factors. The field of neural tissue transplantation as a productive treatment protocol for neurodegenerative disorders has received much attention resulting in its progression to clinical trials. To date the major problem with this field has been the lack of ability to obtain enough viable cells. The present invention provides a method of maintaining such tissue in a state that will prevent them from losing their ability to serve as an appropriate graft for neurodegenerative diseases.

Methods of grafting cells are now well known to those of skill in art (U.S. Pat. Nos. 5,762,926; 5,650,148; 5,082,670). Neural transplantation or grafting involves transplantation of cells into the central nervous system or into the ventricular cavities or subdurally onto the surface of a host brain. Conditions for successful transplantation include: 1) viability of the implant; 2) retention of the graft at the site of transplantation; and 3) minimum amount of pathological reaction at the site of transplantation.

Methods for transplanting various nerve tissues, for example embryonic brain tissue, into host brains have been described in Neural Grafting in the Mammalian CNS, Bjorklund and Stenevi, eds., (1985) Das, Ch. 3 pp. 23–30; Freed, Ch. 4, pp. 31–40; Stenevi et al., Ch. 5, pp. 41–50; Brundin et al., Ch. 6, pp. 51–60; David et al., Ch. 7, pp. 61–70; Seiger, Ch. 8, pp. 71–77 (1985), incorporated by reference herein. These procedures include intraparenchymal transplantation, i.e. within the host brain (as compared to outside the brain or extraparenchymal transplantation) achieved by injection or deposition of tissue within the host brain so as to be opposed to the brain parenchyma at the time of transplantation (Das, supra).

The two main procedures for intraparenchymal transplantation are: 1) injecting the donor cells within the host brain parenchyma or 2) preparing a cavity by surgical means to expose the host brain parenchyma and then depositing the graft into the cavity (Das, supra). Both methods provide parenchymal apposition between the graft and host brain tissue at the time of grafting, and both facilitate anatomical integration between the graft and host brain tissue. This is of importance if it is required that the graft become an integral part of the host brain and to survive for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord.

The donor cells may also be introduced into the putamen, nucleus basalis, hippocampus cortex, striatum or caudate regions of the brain, as well as the spinal cord.

For grafting, the cell suspension is drawn up into the syringe and administered to anesthetized graft recipients. Multiple injections may be made using this procedure. The age of the donor tissue, i.e., the developmental stage, may affect the success of cell survival after grafting.

The cellular suspension procedure thus permits grafting of donor cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^8$ cells are introduced per graft.

For transplantation into cavities, which may be preferred for spinal cord grafting, tissue is removed from regions close to the external surface of the CNS to form a transplantation cavity, for example by removing bone overlying the brain and stopping bleeding with a material such a gelfoam (Stenevi et al., Brain Res. 114:1–20 (1976)). Suction may be used to create the cavity. The graft is then placed in the cavity. More than one transplant may be placed in the same cavity using injection of cells or solid tissue implants.

Grafting of donor cells into a traumatized brain will require different procedures, for example, the site of injury must be cleaned and bleeding stopped before attempting to graft. In addition, the donor cells should possess sufficient growth potential to fill any lesion or cavity in the host brain to prevent isolation of the graft in the pathological environment of the traumatized brain.

Measurement of Phenotype of Cells

In specific embodiments, it may be necessary to monitor the phenotype of the cell that has been grown in the subatmospheric oxygen conditions so as to determine whether differentiation or other modification of the cell has occurred. Various methods may be used to achieve this, including monitoring message level, protein level, subcellular localization, functional assays or morphological changes. The methods for monitoring message level include PCR™ (U.S. Pat. Nos. 5,364,790; 4,800,159; 4,683,195), In situ hybridization (U.S. Pat. Nos. 4,888,278; 4,886,741; 5,506,098; 5,225,326; 5,521,061; 5,538,869; 5,665,540), RNAse protection assay, and single cell PCR™. The methods for monitoring protein level may use antibody staining, HPLC, western blotting or immunoprecipitation. These techniques are all well known to those of skill in the art.

The ability to detect genes that are differentially expressed in two cell types or populations combined with advances of rapid gene detection and sequencing technologies may be used to compare gene expression in cells cultured under varying oxygen concentrations.

Methods of differential display have been used to elucidate the genes responsible for a difference in phenotypes between two relatively similar cell types or during sequential changes of a cell from one state to another. For example, using the differential display technique, Kocher et al. (1995) selected for genes that were up-regulated in renal cell carcinoma compared with normal renal parenchyma. Through this method, Kocher et al. (1995) were able to isolate a gene (DD96) that was rarely expressed in normal epithelial cell populations, expressed diffusely in malignant epithelial cells of the wide majority of carcinomas, and markedly overexpressed in carcinomas originating from the colon, breast, and lung. A similar technique can be used to compare gene expression in cells incubated under traditional versus low oxygen level conditions. Genes up-regulated in one population over the other then may be used as a probe to screen for expression of that gene in other cell populations or the same cell population under different culturing conditions (i.e., in the presence of compounds or environmental stimuli that may affect the expression of the gene).

Kang et al. (1998) have developed a reciprocal subtraction differential RNA display (RSDD) method that permits the rapid and efficient identification and cloning of both abundant and rare differentially expressed genes. The technology was used to analyze gene expression alterations resulting during cancer progression as adenovirus-transformed rodent cells developed an aggressive transformed state (Kang et al., 1998). The approach resulted in the identification and cloning of known and unknown sequences that displayed expression as a function of progression and suppressed expression as a function of progression (Kang et al., 1998). The RSDD technique may be used to compare gene expression between cells during maintenance, proliferation and/or differentiation of the cells from progenitor or stem cells to fully differentiated cells in room air versus subatmospheric conditions.

The methods of differential display may be used in conjunction with rapid DNA sequencing and detection methods, allowing for the ability to screen for or sequence a large number of genes in a relatively short amount of time. U.S. Pat. No. 5,800,992 provides methods for detecting the differential expression of a plurality of genes between two cell types using complimentary polynucleotides in an array. Such technology is commonly referred to as "DNA chip" technology because the polynucleotides are deposited on a substrate that resemble computer microprocessor chips. Also described are methods of sequencing genes using DNA chips.

Additionally, similar techniques are described in U.S. Pat. No. 5,834,181 which utilizes similar technology to detect minor alterations in genes such as single nucleotide substitution, allowing detection of mutations in genes that lead to a change in the phenotype of a cell.

Single-cell reverse transcriptase-polymerase chain reaction (RT-PCR) technique, also will be useful in monitoring the phenotype of the cells grown in the present invention. Such a technique is described by, for example, Cornelison and Wold (1997).

The single cell RT-PCR technique of Cornelison and Wold allows determination of expression of a number of genes at one time and may be used to identify skeletal muscle satellite cells and determine their activation state when incubated in the low/physiological oxygen conditions of the present invention.

Another detection method commonly used is an RNAse protection assay in which a radiolabeled RNA probe is mixed with a test RNA population, such as total cellular RNA from an individual, under conditions where complementary segments of the RNA probe and the test RNA will hybridize. RNAse is then added to the mixture to destroy unprotected (unhybridized), single-stranded probe and test RNA. When all single-stranded RNA has been destroyed, only short fragments of protected RNA remains that can be analyzed electrophoretically to diagnose the particular RNA composition of the test RNA. The protected double-stranded RNA fragments are denatured before analysis, to make available the detectable, labeled single stranded RNA probe fragment.

Disease Models

Once a particular set of cells have been generated it will of course be necessary to test that these cells would apply to a disease model. Animal models of Parkinson's Disease and other neurodegenerative diseases are now well known to those of skill in the art.

For example, a rat model of Parkinson's disease can be created by giving a unilateral injection of saline-ascorbate 6-hydroxy-dopamine (6-OHDA) into the medial forebrain bundle. This produces a lesion that ultimately mimics Parkinsonian behavior. Completeness of the lesion produced can be determined by monitoring either apomorphine or amphetamine induced rotational behavior (Ungerstedt and Arbuthnott, 1970). Animals turning at a rate of more than 7 turns per minute (Schmidt et al., 1982) can be inferred to have the appropriate lesion (at least 7 contralateral rotations/min following apomorphine administration and at least 7 ipsilateral rotations/min towards the side of the lesion following amphetamine administration).

Using such a model a baseline rotation behavior can be established. After that, the cells grown in the present invention can then be transplanted into the rat model as described herein above. Any decrease in the rotational behavior would be indicative of the cellular transplant having an appropriate therapeutic value.

Gene Replacement/Augmentation Applications

Optionally, the CNS cells obtained using the method of the present invention can be manipulated to express desired gene products. Gene therapy can be used to either modify a cell to replace a gene product, to facilitate regeneration of tissue, to treat disease, or to improve survival of the cells following implantation into a patient (i.e. prevent rejection).

In this embodiment, the CNS cells are transfected prior to expansion and differentiation. Techniques for transfecting cells are known in the art.

A skilled artisan could envision a multitude of genes which would convey beneficial properties to the transfected cell or, more indirectly, to the recipient patient/animal. The added gene may ultimately remain in the recipient cell and all its progeny, or may only remain transiently, depending on the embodiment. For example, genes encoding tyrosine hydroxylase, or a monoamine transporter such as VMAT 1 or VMAT 2 could be transfected into certain CNS cells to provide an appropriate therapeutic cell suitable for grafting into a subject with Parkinson's disease. Other genes that could be used include GABA-decarboxylase, enkephalin, dopa decarboxylase (AADC), ciliary neuronal trophic factor (CNTF), brain derived neurotrophic factor (BDNF), neurotrophin (NT)-3, NT-4, and basic fibroblast growth factor (bFGF). In some situations, it may be desirable to transfect the cell with more than one gene. Of course the above therapeutic genes are only exemplary and those of skill in the art will understand that any neurodegenerative disorder that results from an aberration in gene expression and/or function can be treated by gene replacement and/or augmentation. Such disorders and their related genes are well known to those of skill in the art.

In some instances, it is desirable to have the gene product secreted. In such cases, the gene product preferably contains a secretory signal sequence that facilitates secretion of the protein.

The viral vectors used herein may be adenoviral (U.S. Pat. Nos. 5,824,544; 5,707,618; 5,693,509; 5,670,488; 5,585, 362; each incorporated herein by reference), retroviral (U.S. Pat. Nos. 5,888,502; 5,830,725; 5,770,414; 5,686,278; 4,861,719 each incorporated herein by reference), an adeno-associated viral (U.S. Pat. Nos. 5,474,935; 5,139,941; 5,622, 856; 5,658,776; 5,773,289; 5,789,390; 5,834,441; 5,863, 541; 5,851,521; 5,252,479; each incorporated herein by reference), an adenoviral-adenoassociated viral hybrid (U.S. Pat. No. 5,856,152 incorporated herein by reference), a lentiviral vector, a vaccinia viral or a herpesviral (U.S. Pat. Nos. 5,879,934; 5,849,571; 5,830,727; 5,661,033; 5,328, 688; each incorporated herein by reference) vector.

Delivery of the expression constructs through non-viral vectors also is contemplated. Such delivery may employ microinjection (U.S. Pat. No. 5,612,205), electroporation (U.S. Pat. Nos. 5,507,724; 5,869,326; 5,824,547; 5,789,213; 5,749,847; 5,019,034; Tur-Kaspa et al., 1986; Potter et al., 1984), calcium phosphate coprecipitation (Graham and Van Der Eb, 1973; Chen and Okayama, 1987; Rippe et al., 1990), DEAE dextran introduction (Gopal, 1985), receptor mediated introduction (Wu and Wu, 1987; Wu and Wu, 1988), liposome mediated introduction (U.S. Pat. Nos. 5,631,018; 5,620,689; 5,861,314; 5,855,910; 5,851,818; 5,827,703; 5,785,987; Nicolau and Sene, 1982; Fraley et al., 1979), dendrimer technology (U.S. Pat. Nos. 5,795,581; 5,714,166; 5,661,025), naked DNA injection (Harland and Weintraub, 1985) and particle bombardment (U.S. Pat. Nos. 5,836,905; 5,120,657; Yang et al., 1990).

The desired gene is usually operably linked to its own promoter or to a foreign promoter which, in either case, mediates transcription of the gene product. Promoters are chosen based on their ability to drive expression in restricted or in general tissue types, or on the level of expression they promote, or how they respond to added chemicals, drugs or hormones. Particularly contemplated promoters include but are not limited to CMV IE, SV40 IE, β-actin, collagen promoter, TH promoter, AADC promoter and the nestin promoter.

Other genetic regulatory sequences that alter expression of a gene may be co-transfected. In some embodiments, the host cell DNA may provide the promoter and/or additional regulatory sequences.

Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primary the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Application to Other Cell Types

Although the majority of the discussion above is focused on the growth and culturing of CNS cells, it should be appreciated that techniques of the present invention also will be useful for growth of other types of cells. As such it is contemplated that the techniques provided herein will be useful for growing any cells that are routinely used in transplant therapies. For example, such cells may be islets cells for diabetes; myoblasts for muscular dystrophy; hepatocytes for liver disease; skin grafts for wound healing and/or burns, and bone marrow or stem cells for hematopoietic and genetic disorders. In addition, the disclosure of U.S. Pat. No. 6,184,035 (specifically incorporated herein by reference) will provide additional examples that may be useful in conjunction with the present invention.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Material and Methods

Culture of CNS Stem Cells. Animals were housed and treated following NIH guidelines. Cells dissected from rat embryonic lateral ganglionic eminence (E14) or mesencephalon (E12) were mechanically dissociated, plated on plastic 24-well plates (Costar) or 12 mm glass cover slips (Carolina Biologicals) precoated with polyornithine/fibronectin, and grown in defined medium with bFGF (Studer et al., 1998; Johe et al., 1996). In general, bFGF was withdrawn from the medium after 4–6 days of culture. Clonal assays were carried out in plastic 48-well plates (Costar). In some studies, recombinant human (rh)EPO, rhVEGF$_{165}$ or recombinant mouse (rm)FGF8b, or their neutralizing antibodies (all from R&D Systems) were added to cultures at the following concentrations: EPO 0.5 U/ml, EPO neutralizing antibody 10 µg/ml, FGF8 250 ng/ml, FGF8b neutralizing antibody 5 µg/ml, VEGF 50 ng/ml, VEGF neutralizing antibody 0.5 µg/ml. Dose response for EPO was carried out at 0.05 U/ml, 0.5 U/ml, 5 U/ml and 15 U/ml; for anti-EPO at 10 µg/ml and 100 µg/ml. Results of all experiments were confirmed by at least 2 independent culture series.

Low oxygen culture. Cultures were placed in humidified portable isolation chambers (Billups-Rothenberg, Del Mar Calif.), flushed daily with a gas mixture 1% $O_2$, 5% $CO_2$+ 94% $N_2$. Precise $O_2$ levels in the surrounding atmosphere depended on the length of chamber flush (90 sec at 15 L/min achieved 6% $O_2$, 6 minutes of flush achieved 1.5% $O_2$), which was not standardized until availability of an $O_2$-sensitive electrode system (OS2000, Animus Corp., Frazer Pa.). Thus "lowered $O_2$" conditions represent a range of ambient $O_2$ of 3±2%, which approximates normal brain tissue levels (Table 1). The entire chamber was housed in an incubator to maintain temperature at 37° C.

BrdU uptake and TUNEL analysis. Bromodeoxyuridine (10 µM) was added to cultures for exactly 60 minutes, just prior to fixation. Anti-BrdU staining was performed according to the manufacturer's protocol (Amersham Life Sciences). The TUNEL reaction (Boehringer-Mannheim) was also performed according to manufacturer's protocol. TUNEL+ cells were visualized by metal-enhanced DAB reaction (Pierce) after peroxidase conversion of the FITC label.

Immunohistochemistry. Cells were fixed in 4% paraformaldehyde+0.15% picric acid/PBS. Standard immunohistochemical protocols were followed. The following antibodies were used: Stem cell/progenitor characterization: Nestin polyclonal #130 1:500 (Martha Marvin & Ron McKay), PSA-NCAM, En1 and FP4 (all monoclonal 1:2, Developmental Studies Hybridoma Bank, provided by Tom Jessel). Stem cell differentiation: β-tubulin type III (Tuj1) monoclonal 1:500 and polyclonal 1:500 (both BabCO), O4 monoclonal 1:5 (Boehringer-Mannheim), galactocerebroside (GalC) monoclonal 1:50 (Boehringer-Mannheim), glial fibrillary acidic protein (GFAP) 1:100 (ICN Biochemicals). Neuronal subtype differentiation: Tyrosine hydroxylase (TH) polyclonal 1:200–1:500 (PelFreeze, Rogers Ak.) or monoclonal 1:2000 (Sigma), GABA polyclonal 1:500 (Sigma), glutamate 1:500 (Sigma), dopamine-β-hydroxylase (DBH) 1:100 (Protos Biotech Corp). Appropriate fluorescence-tagged (Jackson Immunoresearch) or biotinylated (Vector Laboratories) secondary antibodies followed by metal-enhanced DAB reaction (Pierce) were used for visualization.

Cell Counts and Statistical Procedures. Uniform random sampling procedures were used for cell counts and quantified using the fractionator technique (Gundersen, et al., 1988). Statistical comparisons were made by ANOVA with posthoc Dunnett test when more than 2 groups were involved. If data were not normally distributed, a non-parametric test (Mann-Whitney U) was used to compare lowered vs. 20% $O_2$ results. Data are expressed as mean±SEM.

Reverse-phase HPLC determinations of dopamine content. Culture supernatants of medium, HBSS, and HBSS+56 mM KCl were stabilized with orthophosphoric acid and metabisulfite, and stored at –80° C. until analysis. Stabilization, aluminum adsorption, equipment, and elution of dopamine have been previously described (Studer et al., 1998; Studer et al., 1996). Results were normalized against dopamine standards at varying flow rates and sensitivities.

Western blots. Cell pellets were stored at –80° C. Pellet was lysed in 20 mM Hepes, pH 7.6, 20% glycerol, 10 mM NaCl, 1.5 mM $MgCl_2$, 0.2 mM EDTA, 0.1% Triton-X-100, with protease inhibitors (COMPLETE, Boehringer-Mannheim), homogenized, and incubated on ice for 1 hr. After centrifugation, supernatant protein concentration was assayed by BCA (Pierce). For western, block was 5% milk in TBST, primary TH antibody (Pel-Freeze, Rogers, Ak.) was used at 1:500, and secondary was HRP-conjugated goat anti-rabbit (Pierce) at 1:5000. Signal was detected with SUPERSIGNAL (Pierce).

RTPCR™. Cultures were washed once in PBS before solubilization in 2 ml (per 6 cm dish) Trizol (Life Technologies) then stored at –80° C. RNA extraction was carried out according to manufacturer's recommendations (Gibco Life Technologies). The SUPERSCRIPT kit (Gibco Life Technologies) was used for reverse transcription of 10 µg RNA per condition. PCR conditions were optimized by varying MgCl concentration and cycle number to determine linear amplification range. Amplification products were identified by size and confirmed by DNA sequencing. TH was kindly provided by Vera Vikodem, NIDDK, 30 cyc., 56° C., 300 bp. For the other products the primer sequences, cycle numbers, and annealing temperatures were as shown in Table 2.

TABLE 2 primer sequences, cycle numbers, and annealing temperatures for PCR

| Identity | Forward primer | Reverse primer | Conditions |
|---|---|---|---|
| GAPDH | CTCGTCTCATAGACAAGATGGTGAAG (SEQ ID NO:1) | AGACTCCACGACATACTCAGCACC (SEQ ID NO:2) | 28 cyc., 59° C., 305bp |
| VHL | CCTCTCAGGTCATCTTCTGCAACC (SEQ ID NO:3) | AGGGATGGCACAAACAGTTCC (SEQ ID NO:4) | 35 cyc., 60° C., 208bp |
| HIF1a | GCAGCACGATCTCGGCGAAGCAAA (SEQ ID NO:5) | GCACCATAACAAAGCCATCCAGGG (SEQ ID NO:6) | 30 cyc., 59° C., 235bp |
| EPO | CGCTCCCCCACGCCTCATTTG (SEQ ID NO:7) | AGCGGCTTGGGTGGCGTCTGGA (SEQ ID NO:8) | 30cyc., 60° C., 385bp |

TABLE 2-continued primer sequences, cycle numbers, and annealing temperatures for PCR

| Identity | Forward primer | Reverse primer | Conditions |
|---|---|---|---|
| VEGF | GTGCACTGGACCCTGGCTTTACT (SEQ ID NO:9) | CGCCTTGCAACGCGAGTCTGTGTT (SEQ ID NO:10) | 30 cycles, 60° C., 474bp (detects VEGF-1, VEGF-2 AND VEGF-3) |
| Nurr1 | TGAAGAGAGCGGAGAAGGAGATC (SEQ ID NO:11) | TCTGGAGTTAAGAAATCGGAGCTG (SEQ ID NO:12) | 30 cyc., 55° C., 255bp |
| Ptx3 | CGTGCGTGGTTGGTTCAAGAAC (SEQ ID NO:13) | GCGGTGAGAATACAGGTTGTGAAG (SEQ ID NO:14) | 35 cyc., 60° C., 257Bp |
| SHH | GGAAGATCACAAGAAACTCCGAAC (SEQ ID NO:15) | GGATGCGAGCTTTGGATTCATAG (SEQ ID NO:16) | 30 cyc., 59° C., 354bp |
| FGF8 | CATGTGAGGGACCAGAGCC (SEQ ID NO:17) | GTAGTTGTTCTCCAGCAGGATC (SEQ ID NO:18) | 35 cyc., 60° C., 312bp |
| En1 | TCAAGACTGACTACAGCAACCCC (SEQ ID NO:19) | CTTTGTCCTGAACCGTGGTGGTAG (SEQ ID NO:20) | 30 cyc., 60° C., 381bp |
| FGFR3 | ATCCTCGGGAGATGACGAAGAC (SEQ ID NO:21) | GGATGCTGCCAAACTTGTTCTC (SEQ ID NO:22) | 30 cyc., 55° C., 326bp |
| GDNF | according to Moreau et al., 1998 | | |
| BDNF | GTGACAGTATTAGCGAGTGGG (SEQ ID NO:23) | GGGTAGTTCGGCATTGC (SEQ ID NO:24) | 35 cycles, 56° C., 213bp |

Example 2

Results: Lowered $O_2$ Augments Expansion of Striatal and Mesencephalic Precursors E14 rat striatum, widely used for derivation of CNS precursors, cultured in lowered $O_2$ yielded an average 2- to 3-fold more cells than 20% $O_2$ cultures over a wide range of plating densities in the presence of bFGF. (Basic FGF acts as mitogen for stem cells obtained from many regions of the developing brain. The withdrawal of bFGF initiates differentiation to neurons, astrocytes and oligodendrocytes) (FIG. 1). Identical results were obtained with E12 mesencephalic precursors. For all results, data were verified by at least two independent culture series.

Figure 2A:
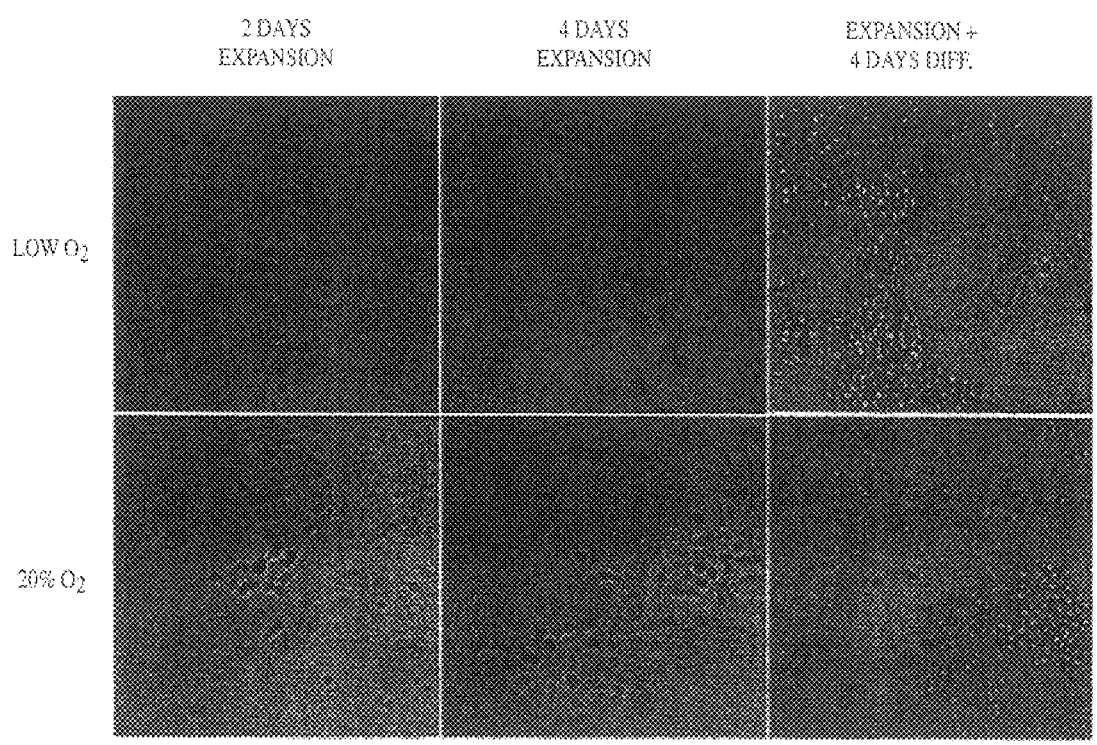
FIG. 2A. Mesencephalic precursors were pulsed with 10 μM BrdU for 60 minutes immediately before fixation, then stained for BrdU uptake. More BrdU+ cells were seen in lowered oxygen cultures during both proliferation and differentiation. Scale bar=20 μm.
Figures 1, 2B:
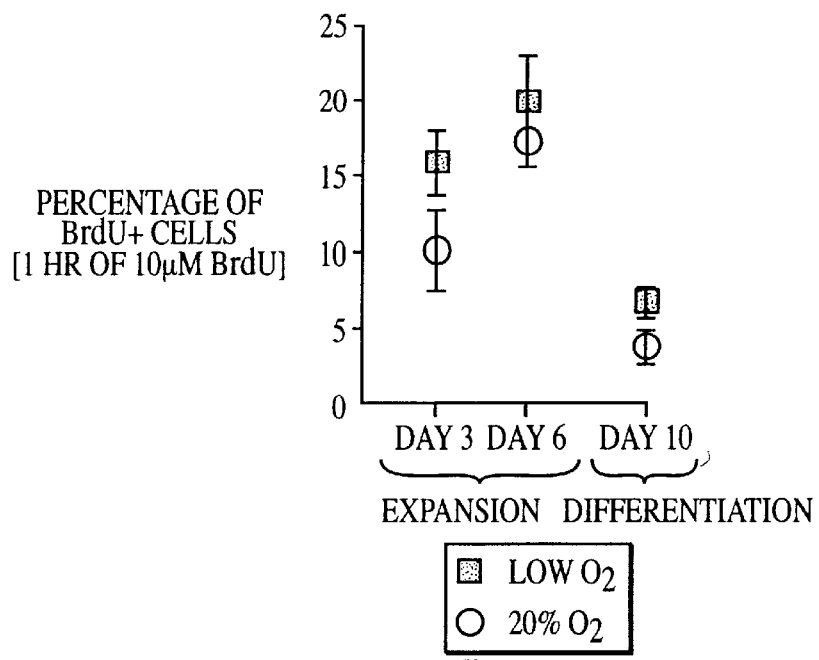
FIG. 2B. Mesencephalic precursors in lowered $O_2$ yielded an increased percentage of BrdU+ cells (FIG. 2B-1) and a greater absolute number of BrdU+ cells (FIG. 2B-2) than cultures maintained at 20% $O_2$. Data are given as mean +/−SEM, n=40. Differences between lowered and 20% $O_2$ were statistically significant at all time points and for all parameters (n=8, p<0.05) except percentage of BrdU+ cells at day 4 of expansion (n=8, p=0.10).
Figures 2, 2B:
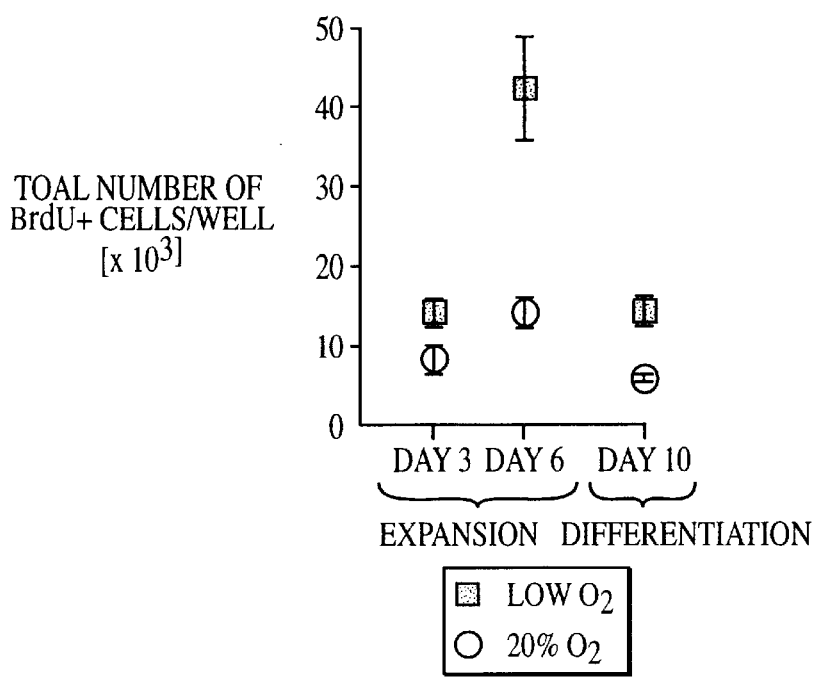
FIG. 2. Lowered oxygen culturing leads to increased proliferation of CNS precursors.

Effects on cell proliferation and cell death. To test whether increased cell yield in lowered $O_2$ is due to increased proliferation, reduced cell death, or both, precursors were pulsed with bromodeoxyuridine (BrdU) for 1 hr immediately before fixation at multiple time points while precursor cells were proliferating or differentiating. Both mesencephalic and striatal precursors showed increased BrdU labeling indices when grown in lowered $O_2$ as compared to traditional cultures. Lowered $O_2$ increased the BrdU labeling index in the presence of bFGF and during cell differentiation following mitogen withdrawal from mesencephalic precursors (FIG. 2). BrdU incorporation rates for striatal precursors showed similar patterns {Day 2 of expansion: 18±6% in lowered $O_2$ vs. 11±6% in 20% $O_2$ (n=24, p<0.05). Day 6 of expansion: 30±8% in lowered $O_2$ vs. 22±5% in 20% $O_2$ (n=24, p<0.05). Day 4 of differentiation (10 days in vitro): 12±5% in lowered $O_2$ vs. 3±3% in 20% $O_2$ (n=24, p<0.05)}.

Figure 3A:
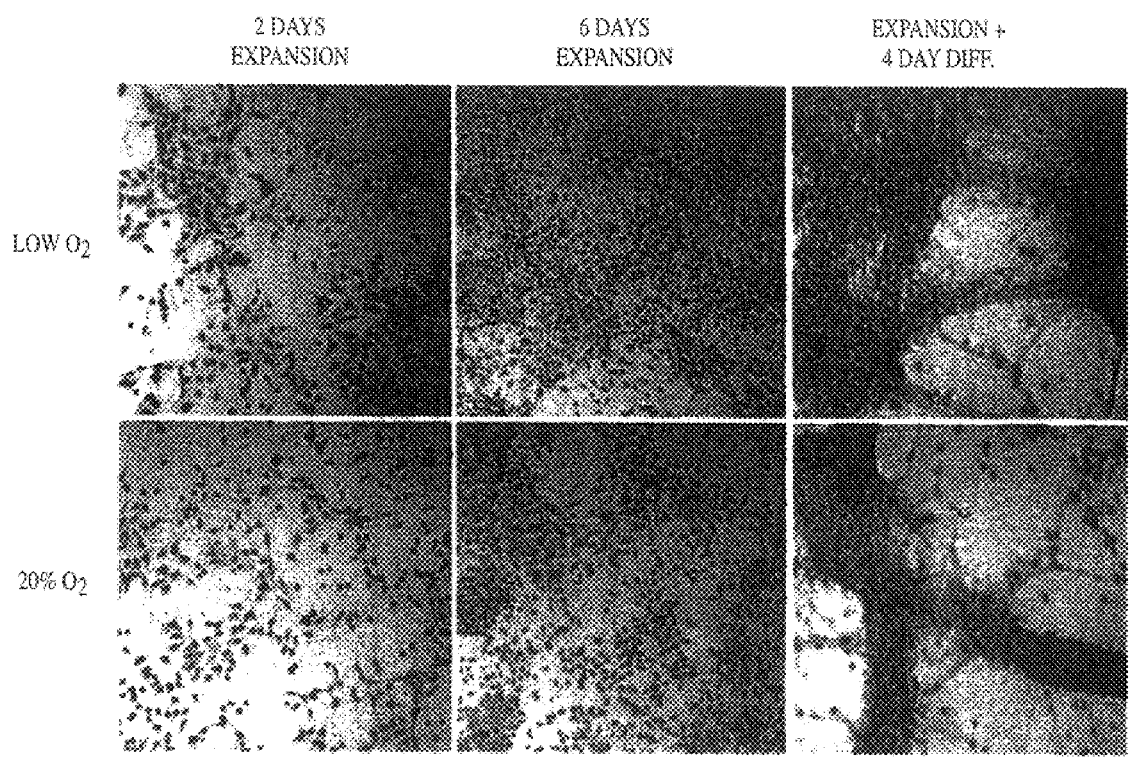
FIG. 3A. Apoptosis was assayed by TUNEL labeling of mesencephalic precursors cultured in parallel at either lowered or 20% $O_2$. Representative figures of the expansion phase (2 and 6 days of culture) and the differentiation phase (4 days after bFGF withdrawal) are shown. Scale bar=20 μm.
Figure 3B:
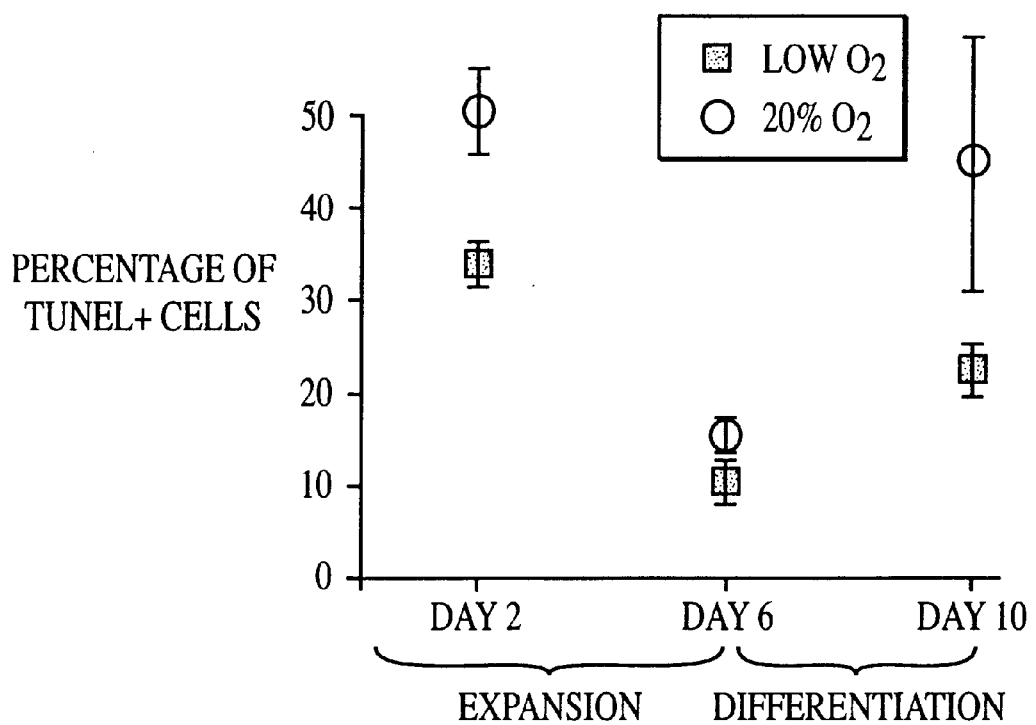
FIG. 3B. Precursors grown at lowered $O_2$ showed a significant decrease in the percentage of apoptotic cells (n=8, p<0.05) compared to traditional cultures.

In addition to this apparent increase in cell proliferation in lowered $O_2$ cultures, precursor cells were also less likely to undergo apoptosis than CNS precursors grown in 20% $O_2$. Both mesencephalic and striatal precursors revealed significantly reduced percentages of TUNEL-positive cells both during expansion and after bFGF withdrawal. TUNEL data for mesencephalic precursors are summarized in FIG. 3. Thus, both reduced apoptosis and increased cell proliferation contribute to elevated yield of cells at the end of the expansion phase. Cell death is reduced but not entirely eliminated during the differentiation phase by lowering the $O_2$ levels.

Figure 4A:
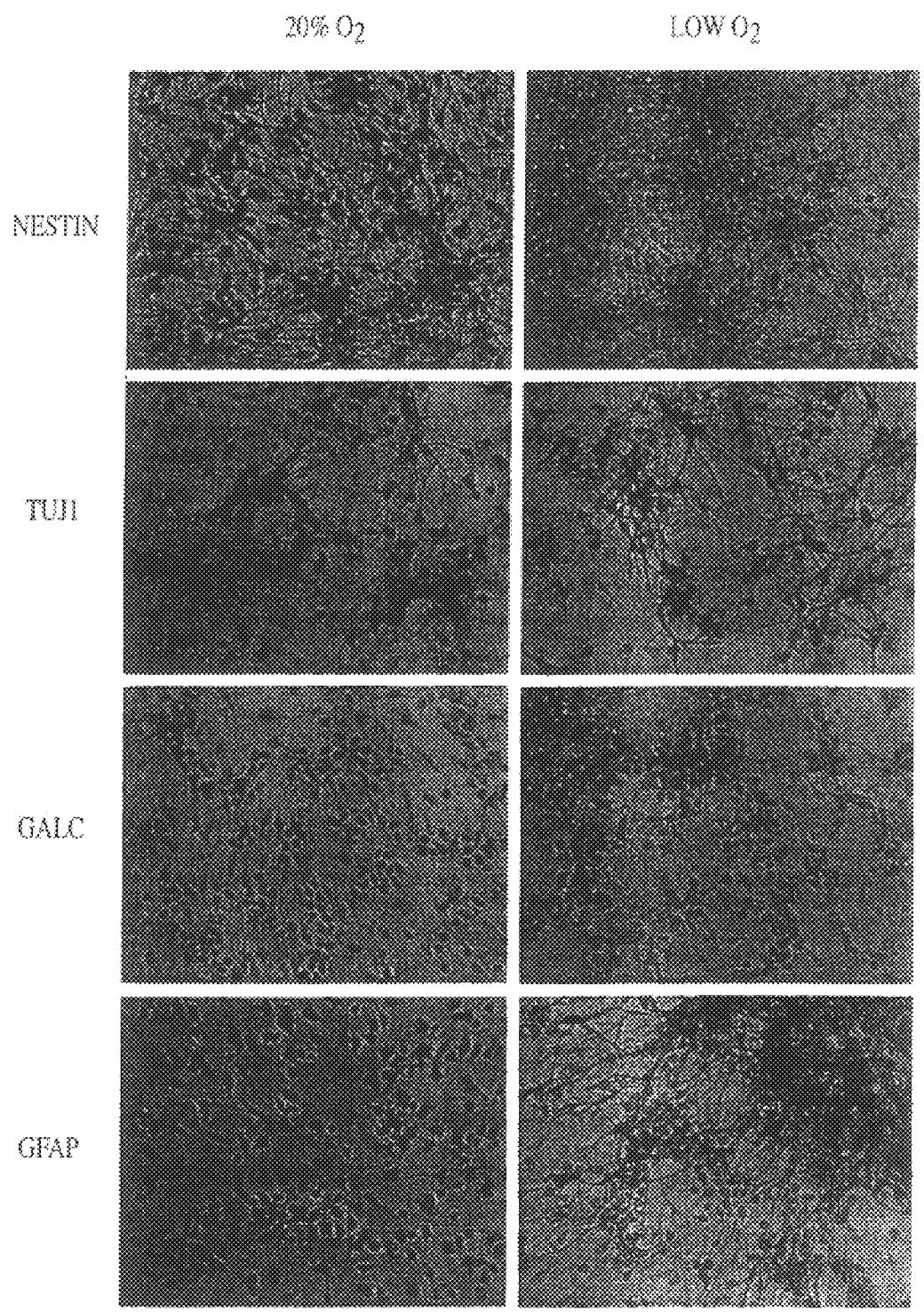
FIG. 4A. Striatal cultures in lowered or 20% $O_2$ were assessed for the relative percentages of precursor-derived neurons (by TUJ1 stain), astrocytes (GFAP) and oligodendrocytes (Gal-C) after 5 days of bFGF proliferation followed by four days of cell differentiation (for quantification see text).
Figure 4B:
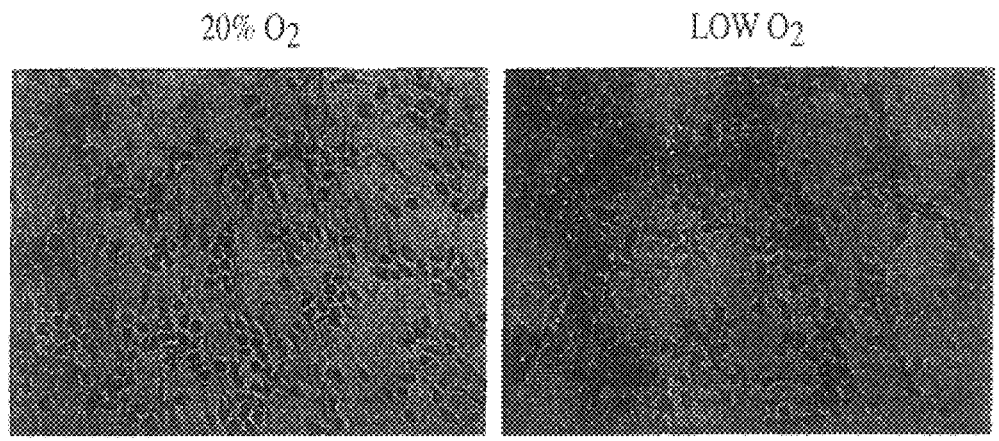
FIG. 4B. Passaged mesencephalic precursors were proliferated for 6 days and differentiated for 5 days in lowered or 20% $O_2$ and analyzed for O4, a marker of oligodendrocyte precursors. O4+ cells could be detected only in lowered oxygen cultures.
Figure 6A:
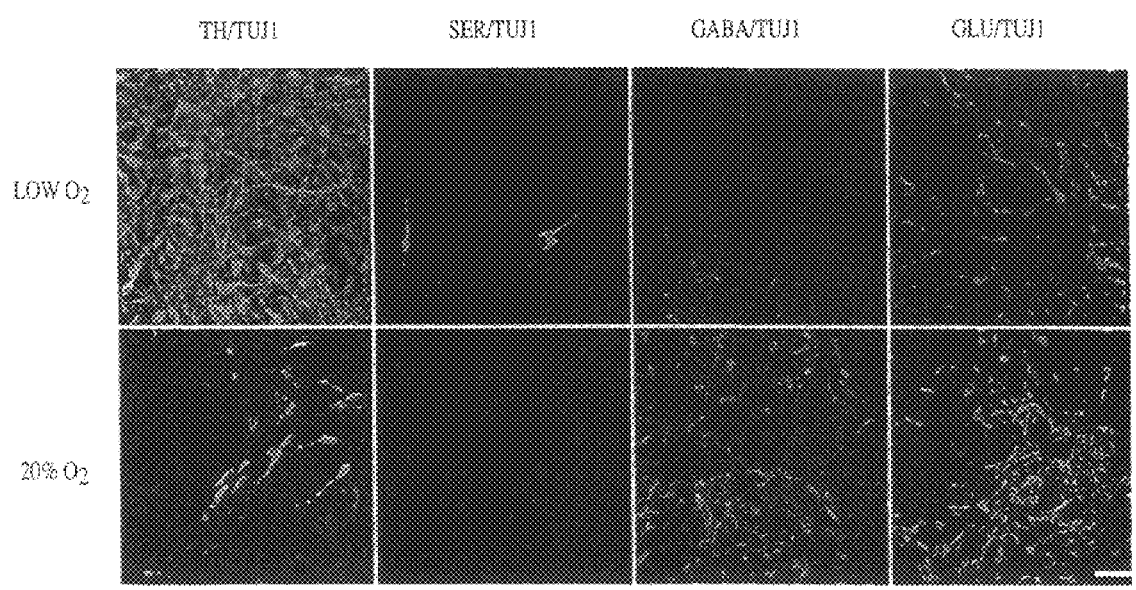
FIG. 6. Neuronal subtype differentiation from mesencephalic precursors in lowered vs. 20% $O_2$. Double immunocytochemical labeling revealed that lowered $O_2$ culturing markedly increased the representation of dopaminergic and serotonergic neuronal (Tuj1+) subtypes, but decreased the representation of GABA+ and Glutamate+ neurons (FIG. 6A). Colony depicted in GABA stain at 20% $O_2$ is an unusual example of very high GABA expression under these conditions. TH and GABA were not co-expressed as seen in some developing neurons in vivo. Floor plate cells (FP4+) were more numerous in lowered $O_2$ cultures as was the percentage of neurons expressing the midbrain transcription factor En1. Precursor markers nestin and PSA-NCAM were both reduced in lowered $O_2$ cultures after differentiation compared to 20% $O_2$ conditions (FIG. 6B). Scale bars=20 μm.
Figure 6B:
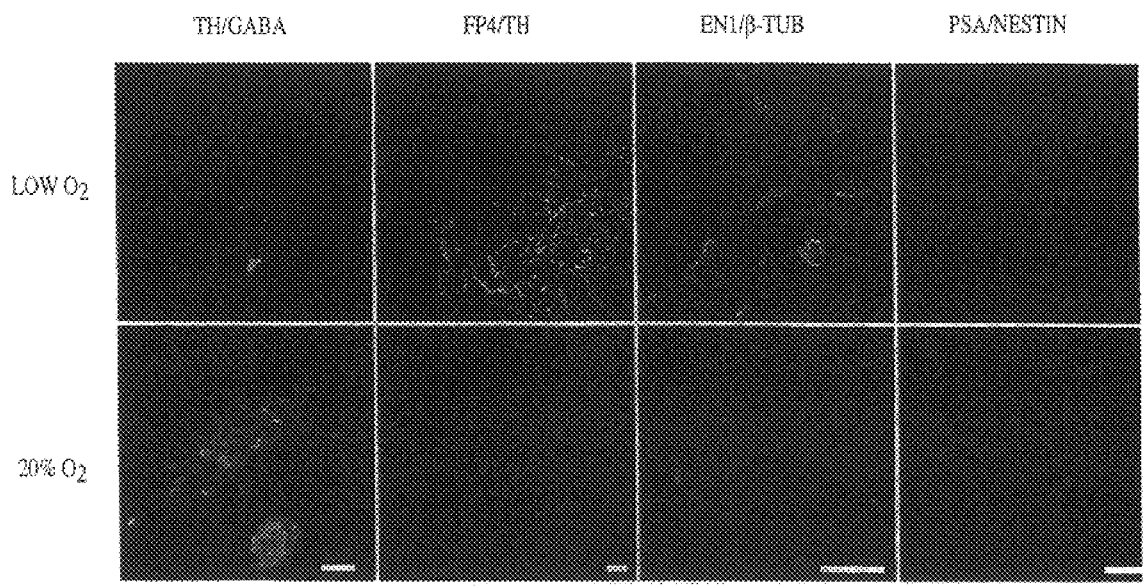

Cell lineage and clonal growth. A series of molecular markers were used, together with morphologic assessment in order to characterize how lowered $O_2$ culturing affects the choice of differentiation pathways and the kinetics of differentiation. Immunoreactivity for the intermediate filament nestin was used to discriminate CNS stem and progenitor cells from more differentiated progeny (Lendahl et al., 1990). Six days after bFGF withdrawal the percentage of nestin-positive cells derived from expanded precursors was grossly reduced in lowered $O_2$ cultures compared with 20% $O_2$ cultures, suggesting that differentiation might have been accelerated in lowered $O_2$ (FIG. 4A and FIG. 6). The sialic acid substituted form of NCAM (PSA-NCAM), a proposed marker for committed neuronal progenitors (Mayer et al., 1997), was conversely reduced in differentiated lowered $O_2$ cultures (FIG. 6). The idea of accelerated progression to a more differentiated phenotype was supported by the earlier appearance of neuronal and glial markers in lowered $O_2$. Neurons were assessed by β-tubulin III (TUJ1) staining, astrocytes by glial fibrillary acidic protein (GFAP), oligodendrocyte precursors by O4, and oligodendrocytes by GalC galactocerebroside staining (FIG. 4). Five days after bFGF withdrawal striatal cultures held at low $O_2$ contained 46% Tuj1-positive cells vs. 34% in 20% $O_2$ (n=12, p<0.05); Six percent were GFAP+ vs. 2% in 20% $O_2$ (n=12, p<0.05); and 4% were Gal-C+ vs. 5% in 20% $O_2$ (p=n.s.). In mesencephalic cultures held at lowered oxygen, 73% were Tuj1+ vs. 63% in 20% $O_2$ (n=12, p=0.06); no GFAP+ cells were detected in either oxygen conditions; 1% were O4+ versus 0% in 20% $O_2$ (n=12, p<0.01) (FIG. 4B).

Figure 4C:
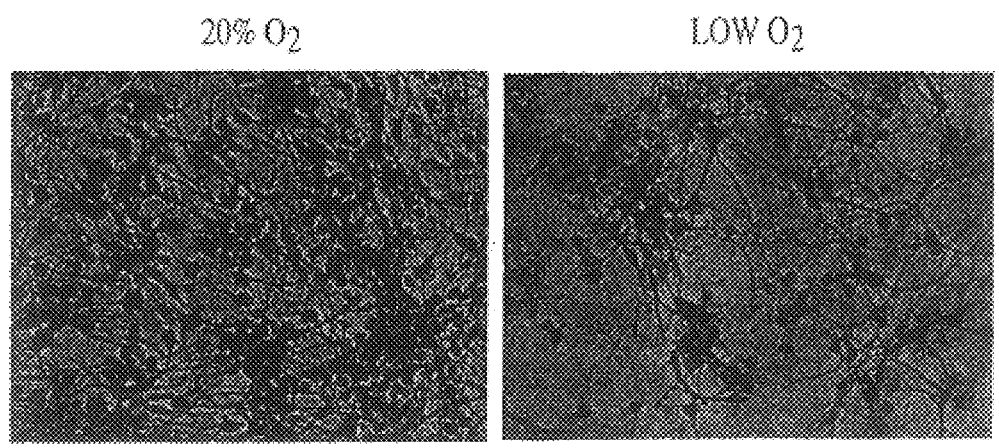
FIG. 4C. Nestin+ clones were derived from single passaged mesencephalic precursor cells after 20 days of bFGF proliferation (left panel). Clones in lowered oxygen differentiated into TUJ1+ neurons upon bFGF withdrawal (right panel).
Figure 4D:
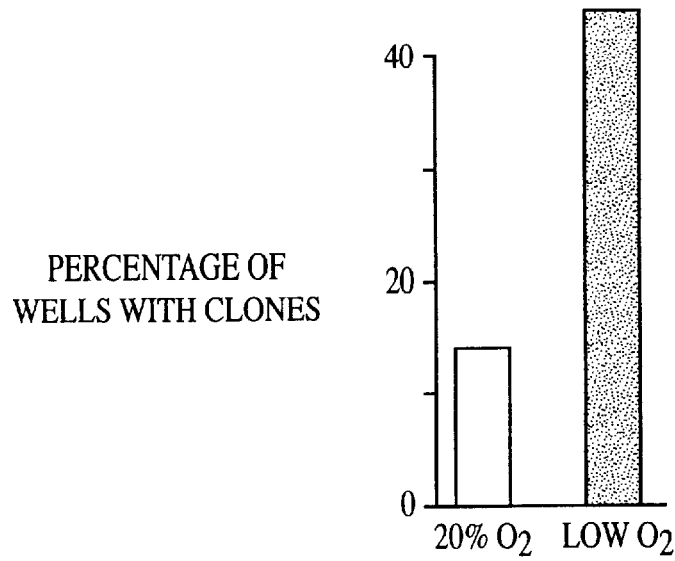
FIG. 4D. Lowered $O_2$ promotes clone formation efficiency. The yield of clones derived from single precursors was 3-fold higher in lowered $O_2$ compared to 20% $O_2$ cultures. The majority of clones derived from precursors in $O_2$ oxygen cultures contained 50–500 cells whereas clone size in 20% $O_2$ cultures was generally 5–50 cells (FIG. 4E). Scale bar=20 μm in all panels.
Figure 4E:
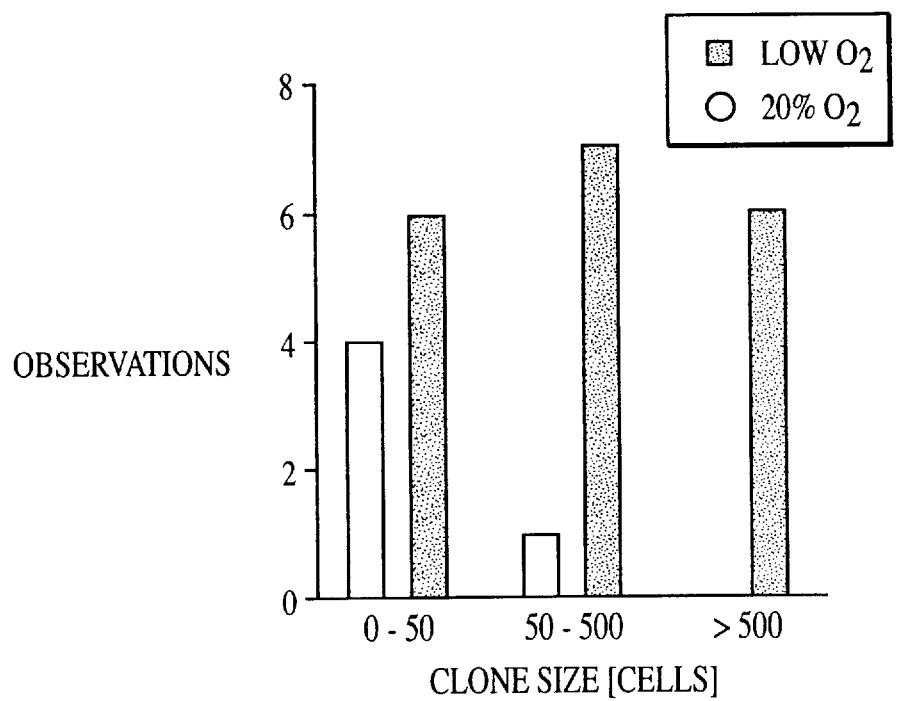
FIG. 4. Basic differentiation patterns of CNS stems in lowered and 20% $O_2$ cultures.

To investigate $O_2$ effects at clonal densities, mesencephalic precursors were first expanded in bFGF for 6 days in 20% $O_2$, replated at a density of 1–5 cells/well, then maintained at either lowered or 20% $O_2$. After 20 days, 20 ng/mL bFGF was withdrawn. Clonal cultures with typical multi-lineage differentiation responses were observed in both lowered and 20% $O_2$ conditions. FIG. 4C illustrates a typical nestin+ clone (left panel) and clonally derived cells undergoing neuronal differentiation 4 days after mitogen withdrawal (right panel). As expected of stem cells, all three lineages were represented in the clones grown in low oxygen conditions. However, the efficiency of clone formation was 3 times higher in lowered $O_2$ and the average clone size also increased from <50 cells in 20% $O_2$ to 50–500 cells in lowered $O_2$ (FIG. 4D, FIG. 4E).

Example 3

Results: Neuronal Subtype Differentiation

Figure 5A:
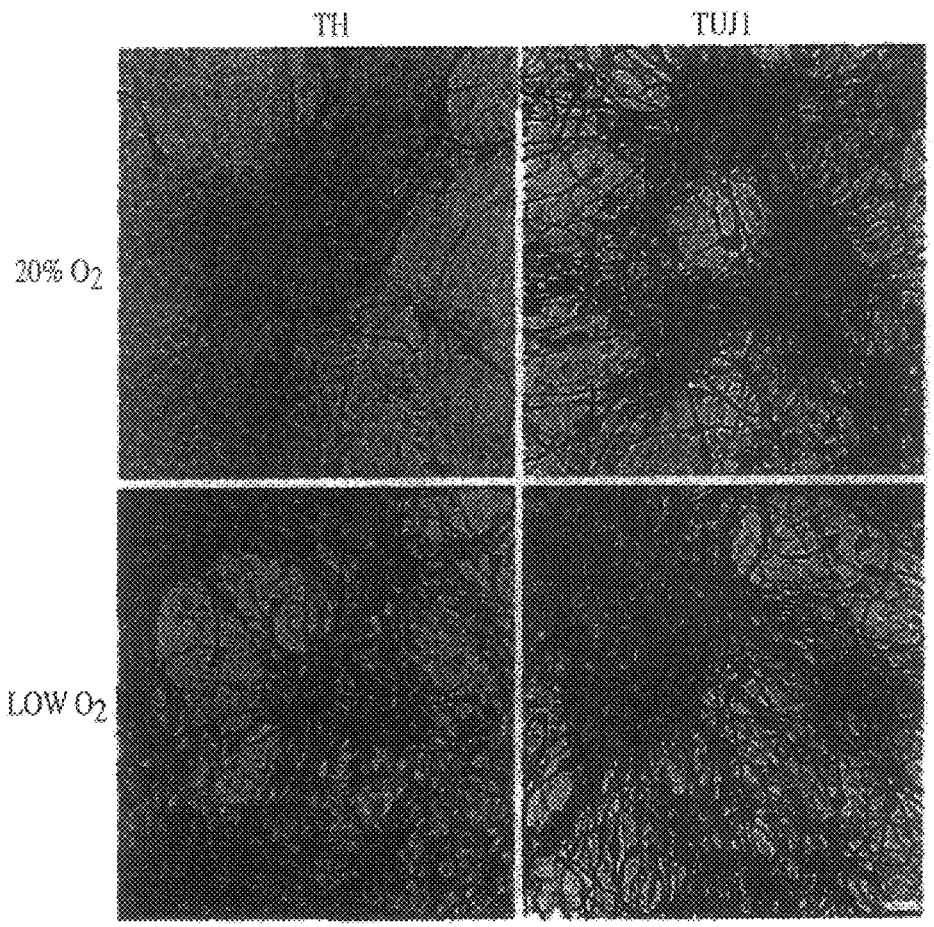
FIG. 5A and FIG. 5B. Precursors from E12 mesencephalon were proliferated with bFGF for 5 days followed by 5 days of differentiation, then stained for the neuronal marker TUJ1 and for TH. A large increase in total number (and percentage) of TH+ neurons was detected (p<0.001) in lowered $O_2$ compared to 20% $O_2$ cultures. Scale bar=20 μm.
Figure 5B:
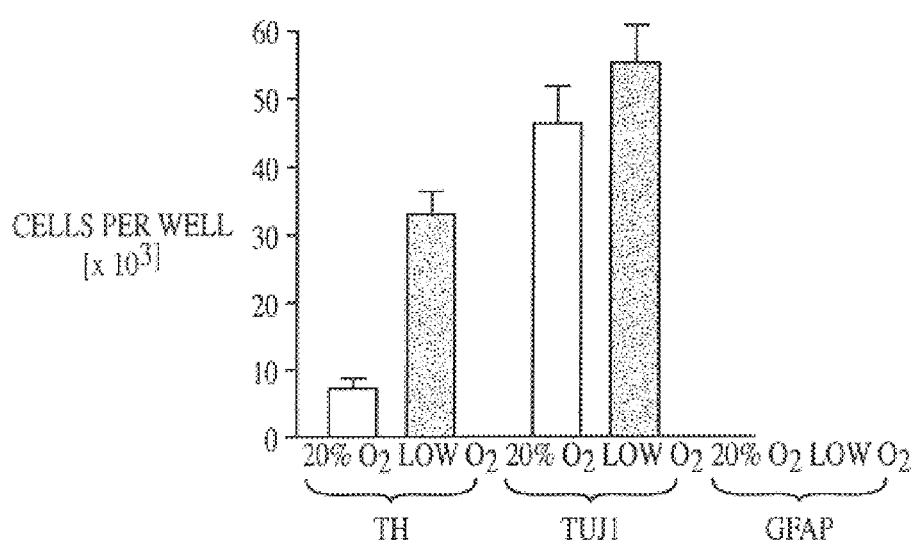
Figure 5C:
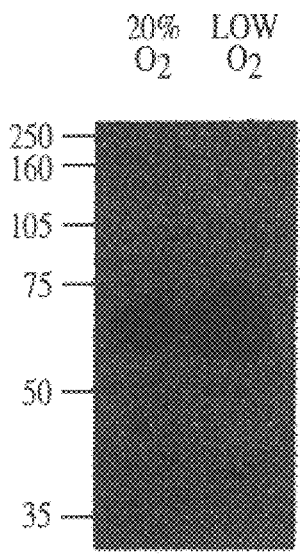
FIG. 5C. Quantification of TH protein level by Western blot analysis revealed significantly more TH in samples from lowered (vs. 20%) $O_2$ cultures. Each lane was loaded with 2.5 m μg total protein.
Figures 2, 5D:
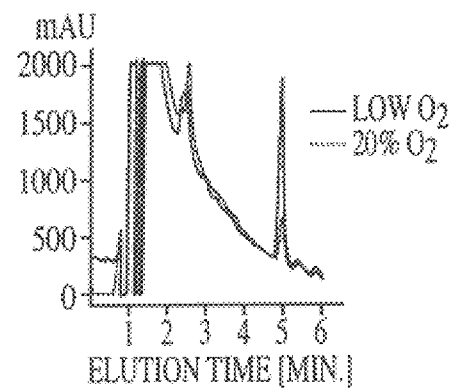
FIG. 5D. rp-HPLC with electrochemical detection was used to quantify dopamine levels in conditioned medium (24 hrs), in HBSS after 15 minutes of conditioning (basal release), and in HBSS+56 mM KCl after 15 minutes (evoked release) (FIG. 5D-1). Significantly more dopamine was detected in cultures maintained at lowered $O_2$ compared to those grown at 20% $O_2$ under all these conditions (conditioned medium p<0.01; basal and evoked release p<0.05).
Figures 1, 5D:
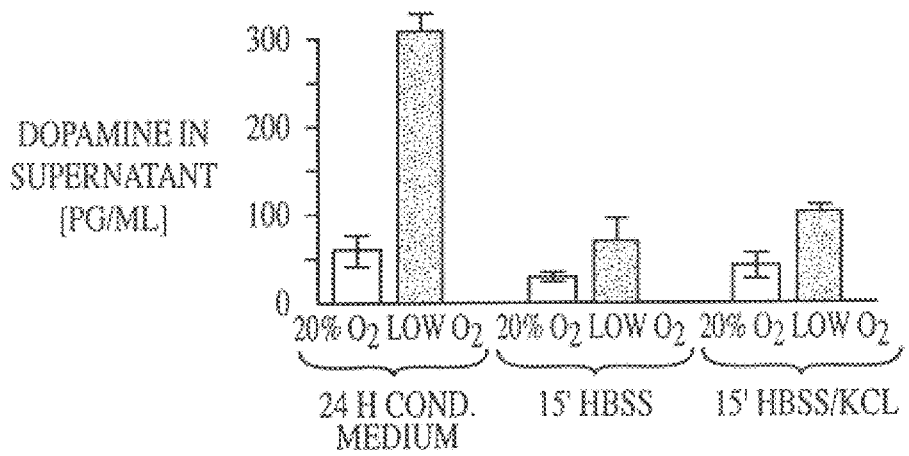

The results above establish that lowered oxygen conditions support stem cell proliferation and differentiation to neurons and glia. The inventors' previous work has shown that nestin-positive mesencephalic precursors differentiate into functional dopaminergic neurons (Studer et al., 1998). Next it was determined whether this specific neuronal fate was influenced by lowered $O_2$. Mesencephalic precursors in lowered oxygen displayed a striking increase in both the absolute number and fraction of neurons expressing TH (FIG. 5A, FIG. 5B). In lowered $O_2$, large neuronal clusters were seen in which virtually all neurons were TH+. On average, 56% of neurons (marked by Tuj1 staining) generated in lowered $O_2$ were TH+ vs. 18% in traditional cultures (n=12, p<0.001). Increased TH-immunoreactivity in lowered $O_2$ cultures correlated with increased TH protein content in Western blots (FIG. 5C). The functional dopaminergic capacity of the TH-positive neurons was further assessed by reverse phase HPLC, which showed significantly increased levels of dopamine in lowered vs. 20% $O_2$ cultures (FIG. 5D): Conditioned medium (24 hours) showed a 5-fold increase in dopamine (n=5, p<0.01). Basal release in HBSS revealed a 2- to 3-fold increase (n=5, p<0.05) and evoked release was 3-fold increased (n=5, p<0.05). These results confirm that lowered oxygen favors the differentiation of functional dopaminergic neurons.

Mesencephalic precursors give rise to neurons with several distinct neurotransmitter phenotypes in addition to dopaminergic fate (Studer et al., 1998). Interestingly, the percentage of serotonergic neurons was also increased in lowered $O_2$, 3.2±1.2% vs. 1.2±0.3% in 20% $O_2$ (n=12, p<0.05, FIG. 6). On the other hand GABA+ and Glutamate+ neurons were less likely to be generated in lowered $O_2$ (FIG. 6: GABA+ cells 6.6±1.8% in lowered $O_2$ vs. 10.4±1.5% n=12, p<0.05; Glutamate+ cells 12.8%±3.8% in lowered $O_2$ cultures vs. 23.6±4.0% in 20% $O_2$ (n=12, p<0.01). No double labeling of TH with GABA was detected indicating that TH immunoreactivity corresponded to differentiated dopaminergic neurons and was not a transient developmental phenomenon seen in developing GABAergic neurons (Max et al., 1996). Furthermore, the TH-positive neurons were not fated to a noradrenergic phenotype, since no dopamine-β-hydroxylase staining could be demonstrated.

Since lowered $O_2$ promoted differentiation of dopaminergic and serotonergic neurons, both ventral neuronal phenotypes (Yamada et al., 1991; Hynes et al., 1995; Ye et al., 1998), it was determined whether these changes were associated with an increase in floor plate cells. Immunohistochemistry revealed expanded zones of FP4+ cells in lowered $O_2$ (FIG. 6). A more striking feature was the increased occurrence of neurons expressing the transcription factor engrailed-1 (En1) in lowered $O_2$ (FIG. 6). Engrailed-1 is critical for normal midbrain development (Joyner, 1996; Danelian and McMahon 1996; Wurst et al., 1994) and has been implicated in control of dopaminergic neuronal fate (Simone et al., 1998).

It is important to establish whether the low oxygen condition enhanced dopaminergic differentiation by acting during the proliferation or differentiation phases of the culture system. Mesencephalic precursors were expanded for 5 days in either lowered or 20% $O_2$. Each group was then subdivided for differentiation in either lowered or 20% $O_2$. Precursors expanded in lowered $O_2$ but differentiated in 20% $O_2$ yielded 38±6% TH+ neurons, similar to those maintained in lowered $O_2$ throughout (41±7%, n=12, p=n.s.) but significantly higher than those maintained in 20% $O_2$ throughout (17±4%, n=12, p<0.01). Exposure to lowered $O_2$ limited to the differentiation phase did not significantly increase the yield of dopaminergic neurons (21±2%, n=12, p=n.s.) compared to cultures maintained in 20% $O_2$ throughout. From these data, it is shown that the major effect of low $O_2$ is during the expansion phase.

Figure 7A:
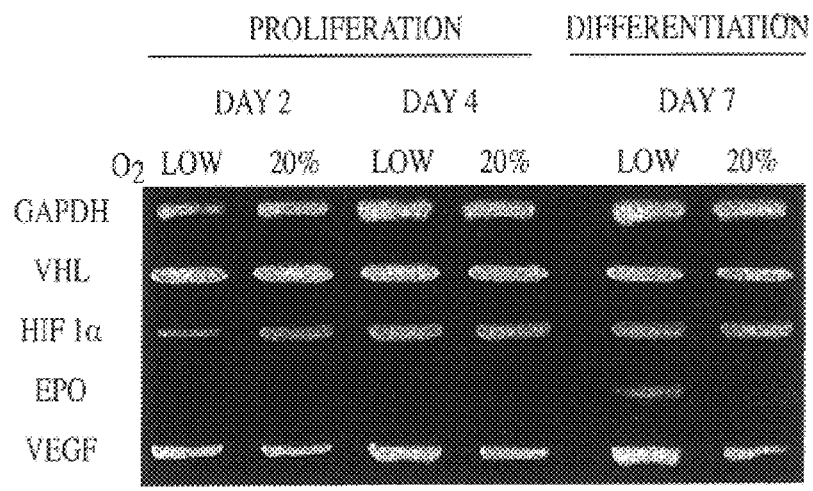
FIG. 7A. Expression of genes involved in the physiological response to changes in oxygen levels. The expression of HIF1α, VHL, EPO and VEGF was assessed after 2 or 6 days of expansion and after differentiation (day 4 of differentiation=day 10 of culture) in lowered and 20% $O_2$. Data are normalized to GAPDH expression. A significant increase in EPO expression was detected in lowered oxygen versus 20% $O_2$ mostly during cell differentiation, whereas VEGF was upregulated during both expansion and differentiation. Surprisingly, no major oxygen-dependent regulation of HIF1α or VHL was observed.
Figure 7B:
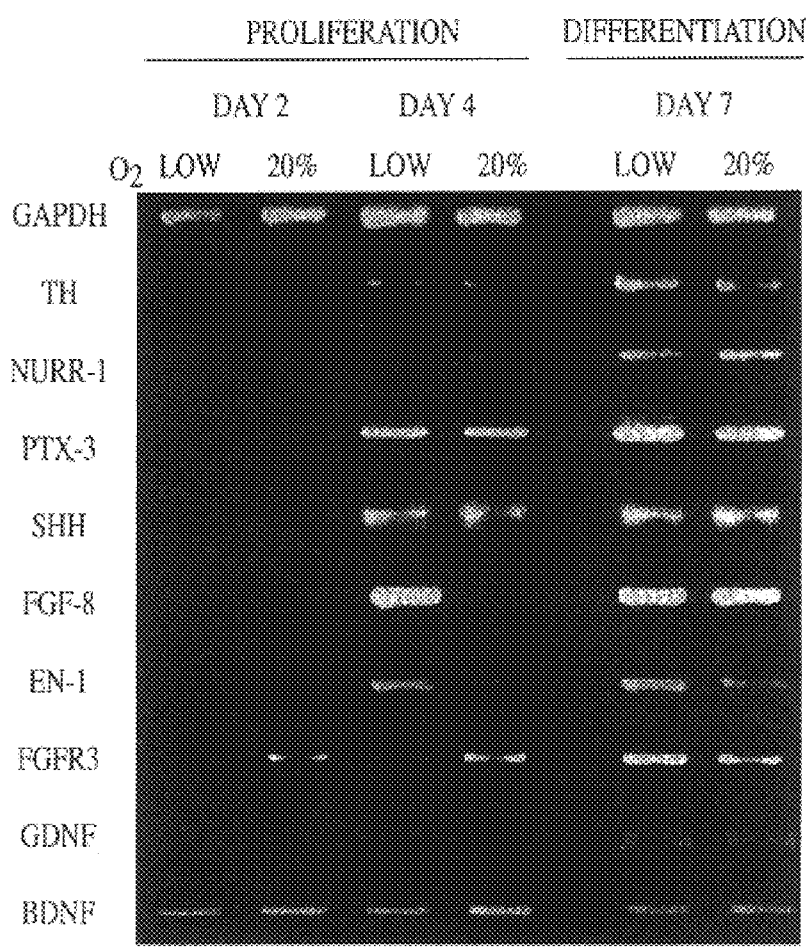
FIG. 7B. Candidate genes involved in midbrain development were also tested for $O_2$-dependent differential expression. Increased expression of TH and Ptx-3 during cell differentiation confirmed the larger number of functional dopaminergic neurons in lowered oxygen cultures (compare FIG. 5). Significant lowered $O_2$-mediated changes in expression levels of FGF8 and En1 were also detected.
Figure 8A:
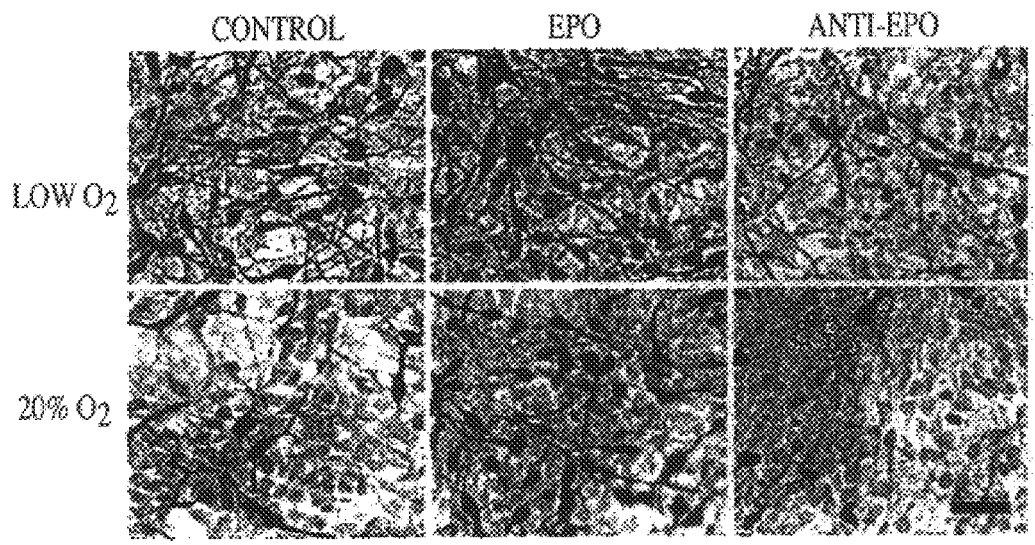
FIG. 8. EPO mimics the lowered oxygen effect on dopaminergic differentiation. Saturating concentrations of EPO or EPO neutralizing antibody were added to E12 mesencephalic precursor cultures during both proliferation and differentiation phase (5 days each) in lowered or 20% $O_2$ (FIG. 8A). EPO supplementation significantly increased TH+ cell numbers in 20% $O_2$ cultures (n=6, p<0.05) (FIG. 8B). EPO neutralizing antibody decreased TH+ cell numbers in both lowered oxygen (n=6, p<0.01) and 20% $O_2$ cultures (n=6, p<0.05) (FIG. 8B). Scale bar=20 μm.
Figure 8B:
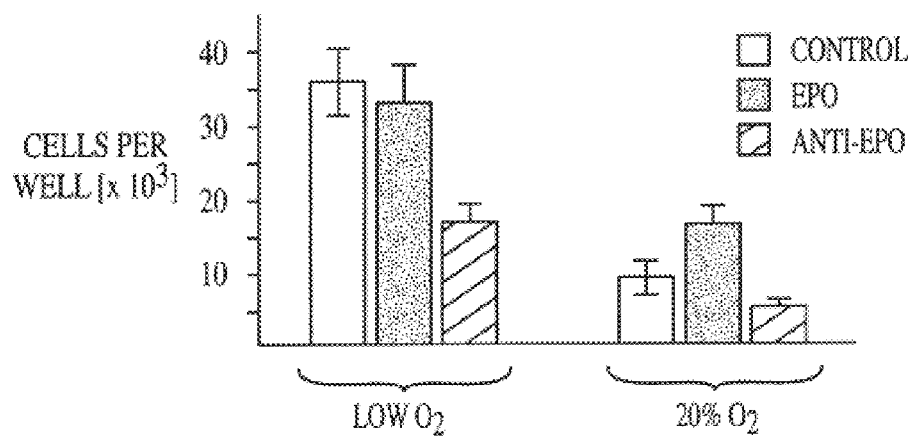

Semi-quantitative RT-PCR was used to assay RNA from cultures at various time points for differential expression of candidate genes involved in dopaminergic neuron development (FIG. 7). A small increase in TH message was detected from lowered $O_2$ cultures after differentiation, compared to 20% $O_2$. The Ptx3 homeobox gene has also been implicated in dopamine neuron development (Smidt et al., 1997) and was also expressed at increased levels in lowered $O_2$ suggesting that these conditions promoted the dopaminergic phenotype, not simply upregulation of TH gene expression. Strong evidence links sonic hedgehog (Echelard et al., 1993); and Nurri (Saucedo-Cardenas et al., 1998) genes to the differentiation of midbrain dopaminergic neurons but no $O_2$-dependent changes in expression were detected. However, engrailed-1 was upregulated in lowered $O_2$, paralleling the immunohistochemical results (FIG. 6). Fibroblast growth factor 8b (FGF8b) message was dramatically upregulated in lowered $O_2$, by the end of the expansion phase. Messages for other regulators of dopaminergic differentiation did not differ significantly between $O_2$ conditions.

Example 4

Discussion: Lowered Oxygen Cultures Favor Proliferation and Survival of CNS Stem Cells Standard conditions for the culture of mammalian cells are 37° C. in a gas atmosphere of 5% $CO_2$ and 95% air. Thus ambient temperature is adjusted to reflect core mammalian body temperature and $CO_2$ is adjusted to reflect approximate venous concentrations, while in striking contrast, $O_2$ levels in culture are not adjusted to reflect physiologic levels. At sea level, unhumidified room air contains 21% $O_2$, and a 95% air/5% $CO_2$ mixture contains 20% $O_2$. Alveolar air contains 14% $O_2$, arterial $O_2$ concentration is 12%, venous $O_2$ levels are 5.3%, and mean tissue intracellular $O_2$ concentration is 3% (Guyton, and Hall, 1996). Directly relating to this study, mean brain $O_2$ in the adult rat and in fetal sheep have both been measured at 1.6% (Silver and Erecinska, 1988; Koos and Power, 1987). Physiological tissue $O_2$ levels in some brain regions are even lower (Table 1). In this work the impact of lowered, more physiologic oxygen levels on CNS stem cell culture was analyzed and showed four major effects: 1) increased proliferation of progenitors; 2) reduced apoptosis; 3) accelerated progression to differentiated states; and 4) elevated absolute number and proportion of TH+-neurons.

Lowered $O_2$ culturing consistently enhanced proliferation of CNS stem cells. A 2- to 4-fold increase in cell number was observed during the proliferation phase when most of the cells are nestin+ precursors. This increase in cell number was also maintained after mitogen withdrawal when proliferation was vastly reduced and differentiation takes place. Although more cells were present in differentiated cultures in lowered $O_2$, the proportions of neurons and glia were similar in the two culture conditions. In neural tissue, there is one supporting, though specialized, precedent for mitogenic activity of lowered $O_2$ in neural crest-derived carotid body chromaffin cells (Nurse and Vollmer, 1997). These dopaminergic glomus cells are functionally specialized $O_2$-sensitive chemoreceptors, and so would be expected to be specifically responsive to changes in $O_2$ levels in the artery. The present results show that lowered oxygen enhances the proliferation and survival of CNS stem cells.

Two specific signaling pathways, FGF8 and EPO, were identified as candidates for significant roles in the lowered $O_2$ response and showed that each can recapitulate part of the lowered $O_2$ phenotype at 20% $O_2$. Lowered $O_2$ culturing led to relative increases in RNAs encoding erythropoietin and FGF8. In early midbrain development, FGF8 functions as a mitogen (Danelian and McMahon 1996), but significant mitogenic or trophic effects of FGF8 on CNS stem cell cultures have not been reported. Here, the increased cell yield from mesencephalic precursors maintained in 20% $O_2$ and exposed to 250 ng/ml FGF8 partly recapitulated the proliferation/trophic effects of lowered $O_2$, with a 30% increase in total number compared to a 200–400% increase in lowered $O_2$. In addition to increased proliferation, less apoptosis occurs in CNS stem cells cultured in lowered $O_2$. There is a potential toxic role for reactive oxygen intermediates (ROI) produced in room air cultures. However, it cannot simply be assumed that 20% $O_2$ cultures generate more oxidative stress than lowered $O_2$ cultures, since free radicals are generated in ischemic conditions (Perez Velazquez et al., 1997).

In contrast to the increased cell number seen in lowered $O_2$, only minor effects were detected on the final ratio of neurons to astrocytes to oligodendrocytes that were derived from expanded striatal or mesencephalic precursors. This result together with clonal analysis confirms that the nestin+ precursors expanded in lowered oxygen have stem cell properties.

Example 5

Discussion: Dopaminergic Commitment and Differentiation

There is a great deal of evidence that CNS stem cells can give rise to multiple neuron types (Johe et al., 1996; Gritti et al., 1996; Kalyani et al., 1998). For several years the midbrain has been studied as model for neuron subtype specification (Hynes et al., 1995;Ye et al., 1998; Wang et al., 1995; Ericson et al., 1995; (reviewed in Hynes and Rosenthal, 1999). Recently, conditions have been established that allow midbrain precursor cells to proliferate and differentiate to dopaminergic neurons in vitro (Studer et al., 1998). In contrast to primary rat fetal mesencephalic cultures where only 5% of the neurons are immunoreactive for TH, this number was increased to 24% of neurons in dissociated precursor cultures from E12 mesencephalon. Here it is shown that 56% of neurons generated from mesencephalic precursors are TH+, and this finding is associated with increased dopamine production by HPLC. Serotonergic neurons, another ventral neuron type found in this region of the brain, were also generated in increased numbers in lowered $O_2$. In contrast the number of GABAergic and Glutamatergic neurons were reduced. The lowered oxygen conditions were most effective in generating dopaminergic neurons during the phase of precursor cell expansion. These results suggest that lowered oxygen conditions enhance the production of ventral fates by a mechanism that acts prior to differentiation.

Transcript levels of FGF8 and En1, accepted mediators of midbrain dopaminergic neuron development (Ye et al., 1998; Simone et al., 1998; Shamim et al., 1999), were upregulated in lowered vs. 20% $O_2$ cultures. FGF8 has also been implicated in the commitment of serotonergic neurons (Ye et al., 1998). These findings are consistent with a role for FGF8 in the expansion of dopaminergic and serotonergic neuronal subtypes seen in lowered $O_2$ cultures. However, addition of FGF8 to 20% $O_2$ cultures or neutralization of FGF8 in lowered $O_2$ cultures did not reproduce the $O_2$-dependent neuronal subtype differentiation patterns. The secreted morphogen sonic hedgehog (SHH) has been shown to induce dopaminergic neuron differentiation in explants of the early neural plate (Hynes et al., 1995; Ye et al., 1998; Wang et al., 1995). Purified sonic hedgehog had no effect on expanded mesencephalic precursors under both oxygen conditions.

Engrailed-1 mRNA and protein levels were increased in lowered oxygen. Engrailed-1 is thought to act in a pathway with pax2, wnt-1 and FGF8 to regulate the fate of midbrain neurons (Joyner, 1996; Danelian and McMahon, 1996; Wurst et al., 1994; Simone et al., 1998). The FGF8 gene contains a binding site for engrailed (Gemel et al., 1999). In addition it was found that the FGF8 5'-UTR sequence (accession #AF065607) contains a 9 base sequence (CCTCCCTCA) that is also known to control oxygen responsiveness in VEGF and EPO regulatory elements (Scandurro, and Beckman, 1998). The inventors have not yet determined if En1 acts as a direct upstream regulator of FGF8 in lowered $O_2$ cultures, or whether they act independently. Nonetheless, the prominent expression of En1 in young neurons (FIG. 6) suggests it may be a good candidate for regulating neuronal subtype differentiation.

EPO levels are known to be regulated by oxygen in the erythropoietic system. EPO and its receptor are expressed in brain from early development through adulthood (Juul et al., 1999), but no specific role for EPO in CNS development has been described. In the adult CNS, however, EPO has received attention as a neuroprotective agent (Sakanaka et al., 1998), and EPO treatment of PC12 cells has been demonstrated to increase intracellular monoamine levels (Masuda et al., 1993). Here the results show that at 20% $O_2$, EPO can mimic part of the lowered $O_2$ effect. Increases in yield of dopaminergic neurons in 20% $O_2$ cultures was dose-dependent, but no additional increase in yield was mediated by EPO in lowered oxygen, suggesting that the EPO levels in lowered $O_2$ were at maximal functional levels for this response. Though EPO supplementation of 20% $O_2$ cultures significantly improves dopaminergic yield, the full effect of lowered $O_2$ could not be recapitulated, suggesting that additional factors are involved in promoting dopaminergic differentiation in lowered $O_2$. Nonetheless, the finding that EPO affects the differentiation patterns of expanded CNS precursors is novel and identifies EPO as a component of increased dopaminergic neuron yield in lowered oxygen conditions.

A recent report highlighted increased dopamine content after differentiated dopaminergic mesencephalic neurons were exposed to hypoxic conditions (0% $O_2$ gas mixture) (Gross et al., 1999). Another study described a relative increase in TH-expressing neurons in primary neuronal cultures from E14 rats after exposure to 5% $O_2$ (Colton et al., 1995). It is also known that hypoxic conditions favor expression of the TH gene (Czyzyk-Krzeska et al., 1994; Paulding, and Czyzyk-Krzeska, 1999). However, this is the first report that lowered oxygen conditions support CNS stem cells during the expansion phase and enhance the production of ventral neuronal subtypes.

Compared to 20% $O_2$ the net expansion of dopaminergic neurons in lowered $O_2$ was at least 9-fold increased (a three-fold increase in total cell numbers, and a 3-fold increase in the percentage of TH+-neurons). HPLC shows that these neurons produce dopamine. The present results show that oxygen levels much lower than those traditionally used in culture may be useful in mimicking in vivo phenomena. Lowered $O_2$ culturing has the practical implication of contributing to a more efficient production of dopaminergic neurons for transplant therapy in Parkinson's disease.

Finally, effects of lowered, more physiological $O_2$ on cell cultures are not limited to the CNS, and extend to the PNS and to other non-neuronal tissues.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bjorklund and Stenevi, Intracerebral neural grafting in animal models of aging brain: strategies, rationale and preliminary results. Dan Med Bull. 32 Suppl 1:35–9 (1985).

Bjorklund, Dopaminergic transplants in experimental parkinsonism: cellular mechanisms of graft-induced functional recovery, Curr Opin Neurobiol. 2(5):683–9 (1992)

Bosio et al., Functional breakdown of the lipid bilayer of the myelin membrane in central and peripheral nervous system by disrupted galactocerebroside synthesis," Proc. Natl. Acad. Sci. U.S.A. 93:13280–13285, 1996.

Bowenkamp et al., Glial cell line-derived neurotrophic factor supports survival of injured midbrain dopaminergic neurons. J Comp Neurol.;355(4):479–89 (1995).

Chen and Okayama, High-efficiency transfection of mammalian cells by plasmid DNA," Mol. Cell Biol., 7:2745–2752, (1987)

Chen et al., The effect of prior in vitro exposure of donor cells to trophic factors in neuro transplantation. Exp. Neurol., 138:64–72. (1996).

Colton et al., Protection from oxidation enhances the survival of cultured mesencephalic neurons. Exper. Neurol. 132, 54–61 (1995).

Cornelison & Wold, "Single-Cell analysis of Regulatory Gene Expression in Quiescent and Activated Mouse Skeletal Muscle Satellite Cells," Developmental Biology, 191:270–283, (1997).

Czyzyk-Krzeska et al., Hypoxia increases rate of transcription and stabiity of tyrosine hydroxylase mRNA in pheochromocytoma (PC 12) cells. J. Biol. Chem. 269, 760–764 (1994).

Danelian, P. S., McMahon, A. P. Engrailed-1 as a target of the Wnt-1 signalling pathway in vertebrate midbrain development. Nature 383, 332–334 (1996).

Dunnett and Bjorkland., in Functional Neural Transplantation, Advances in Neuroscience, Volume 2, Raven Press, New York (1994)

Echelard et al., Sonic hedgehog, a member of a family of putative signaling molecules, is implicated in the regulation of CNS polarity. Cell 75, 1417–1430, (1993).

Engele and Bohn, The neurotrophic effects of fibroblast growth factor on dopaminergic neurons in vitro are mediated by mesencephalic glia. J. Neurosci., 11:3070–3078 (1991).

Ericson et al., Sonic hedgehog induces the differentiation of ventral forebrain neurons: A common signal for ventral patterning within the neural tube. Cell 81, 747–756 (1995).

Fraley et al., "Entrapment of a bacterial plasmid in phospholipid vesicles: Potential for gene transfer," Proc. Natl Acad. Sci. USA, 76:3348–3352, (1979).

Freeman et al., The USF protocol for fetal nigral transplantation in Parkinson's disease Experimental Neurology, 129:6–7(1994).

Gash et al., Functional recovery in Parkinsonian monkeys treated with GDNF. Nature, 380:252–255. (1996).

Gemel et al., Fibroblast growth factor-8 expression is regulated by intronic engrailed and Pbx1-binding sites. J. Biol. Chem. 274, 6020–6026 (1999).

Gopal, "Gene transfer method for transient gene expression, stable transfection, and cotransfection of suspension cell cultures," Mol. Cell Biol., 5:1188–1190, (1985).

Graham and van der Eb, "A new technique for the assay of infectivity of human adenovirus 5 DNA", Virology, 52:456467, (1973).

Gritti et al., Multipotential stem cells from the adult mouse brain proliferate and self-renew in response to basic fibroblast growth factor. J. Neurosci. 16, 1091–1100 (1996).

Gross et al. Hypoxia during early developmental period induces long-term changes in the dopamine content and release in a mesencephalic cell culture. Neuroscience 92, 699–704 (1999).

Gundersen et al., Some new, simple and efficient stereological methods and their use in pathological research and diagnosis. APMIS 96, 379–394 (1988).

Guyton and Hall, "Transport of oxygen and carbon dioxide in the blood and body fluids," In: Textbook of Medical Physiology, WB Saunders Co., Philadephia, 1996, pp. 513–523.

Harland and Weintraub, "Translation of mammalian mRNA injected into Xenopus oocytes is specifically inhibited by antisense RNA," J. Cell Biol., 101: 1094–1099, (1985).

Hazel & Muller, "Culture of Neuroepithelial Stem Cells," Current Protocols in Neuroscience, 3.1.1–3.1.6, (1997).

Hoffman et al., "Comparison of the effect of etomidate and desflurane on brain tissue gases and pH during prolonged middle cerebral artery occlusion." Anesthesiology 88, 1198–1194, 1998.

Hyman et al., BDNF is a neurotrophic factor for dopaminergic neurons of the substantia nigra. Nature, 350:230–232 (1991).

Hynes and Rosenthal, Specification of dopaminergic and serotonergic neurons in the vertebrate CNS. Curr. Opin. Neurobiol. 9, 26–36 (1999).

Hynes et al., Control of neuronal diversity by the floor plate: Contact-mediated induction of midbrain dopaminergic neurons. Cell 80, 95–101 (1995).

Isacson et al., Graft-induced behavioral recovery in an animal model of Huntington's disease. Proc. Natl. Acad. Sci., 83:2728–2732 (1986).

Johe et al., Single factors direct the differentiation of stem cells from the fetal and adult central nervous system. Genes Dev. 10, 3129–3140 (1996).

Joyner, A. L. Engrailed, Wnt, and Pax genes regulate midbrain-hindbrain development. Trends Genet. 12, 15–20 (1996).

Juul et al., Immunohistochemical localization of erythropoietin and its receptor in the developing human brain. Pediatr. Dev. Pathol. 2, 148–158 (1999).

Kalyani et al., Spinal cord neuronal precursors generate multiple neuronal phenotypes in culture. J. Neurosci. 18, 1856–1868 (1998).

Kang et al., Reciprocal subtraction differential RNA display: an efficient and rapid procedure for isolating differentially expressed gene sequences. *Proc. Natl. Acad. Sci. U.S.A.*, 95(23):13788–13793, 1998.

Knusel et al., Selective and nonselective stimulation of central cholinergic and dopaminergic development in vitro by nerve growth factor, basic fibroblast growth factor, epidermal growth factor, insulin and the insulin-like growth factors I and II. *J. Neurosci.*, 10:558–567., (1990).

Knusel et al., Promotion of cholinergic and dopaminergic neuron differentiation by brain-derived neurotrophic factor but not neurotrophin-3. *Proc. Natl. Acad. Sci. USA*, 88:961–965(1991).

Kocher et al., Identification of a novel gene, selectively up-regulated in human carcinomas, using the differential display technique. *Clin. Cancer Res.*, 1(10):1209–1215, (1995).

Koos and Power, Predict fetal brain PO2 during hypoxaemia and anemia in sheep. *J. Develop. Physiol.* 9, 517–726 (1987).

Lendahl et al., CNS stem cells express a new class of intermediate filament protein. *Cell* 60, 585–595 (1990).

Lindvall et al., Grafts of fetal dopamine neurons survive and improve motor function in Parkinson's disease. *Science*, 247:574–577(1990).

Martinez-Serrano et al. CNS-derived neural progenitor cells for gene transfer of nerve growth factor to the adult brain: complete rescue of axotomized cholinergic neurons after transplantation into the septum. *J. Neurosci.*, 15:5668–5680(1996).

Masuda et al., Functional erythropoietin receptors of the cells with neural characteristics—Comparison with receptor properties of erythroid cells. *J. Biol. Chem.* 268, 11208–11216 (1993).

Max et al., Co-expression of tyrosine hydroxylase and glutamic acid decarboxylase in dopamine differentiation factor-treated striatal neurons in culture. *Dev. Brain Res.* 91, 140–142 (1996).

Maxwell et al., The tumour suppressor protein VHL targets hypoxia-inducible factors for oxygen-dependent proteolysis. *Nature* 399, 271–275 (1999).

Mayer et al., Basic fibroblast growth factor promotes the survival of embryonic ventral mesencephalic dopaminergic neurons-I. Effects in vitro. Neuroscience, 56:379–388 (1993a).

Mayer et al., Basic fibroblast growth factor promotes the survival of embryonic ventral mesencephalic dopaminergic neurons-II. Effects on nigral trasnplants in vivo. Neurosci., 56:389–398, (1993b).

Mayer-Proschel et al., Isolation of lineage-restricted neuronal precursors from multipotent neuroepithelial stem cells. *Neuron* 19, 773–785 (1997).

McKay, R. D. Stem cells in the central nervous system. *Science* 276, 66–71 (1997).

Moreau et al., Regulation of c-ret expression by retinoic acid in rat metanephros: implication in nephron mass control. *Am. J. Physiol.* 44, F938-F945 (1998).

Neelakanta & Csete, "Efforts to overcome the liver donor shortage," *Chirurgia Internat.,* 1996.

Neural Grafting in the Mammalian CNS, Bjorklund and Stenevi, eds., 1985 Das, Ch. 3 pp. 23–30; Freed, Ch. 4, pp. 31–40; Stenevi et al., Ch. 5, pp. 41–50; Brundin et al., Ch. 6, pp. 51–60; David et al., Ch. 7, pp. 61–70; Seiger, Ch. 8, pp. 71–77, 1985

Nicolau and Sene, Liposome-mediated DNA transfer in eukaryotic cells, Biochim. Biophys. Acta, 721:185–190, (1982).

Nikkhah et al., Platelet-derived growth factor promotes survival of rat and human mesencephalic dopaminergic neurons in culture. Exp. Brain Res., 92:516–523 (1993).

Nurse and Vollmer, Role of basic FGF and oxygen in control of proliferation, survival, and neuronal differentiation in carotid body chromaffin cells. *Dev. Biol.* 184, 197–206 (1997).

Olanow et al., Fetal nigral transplantation as a therapy for Parkinson's disease. *Trends Neurosci.* 19, 102–109 (1996).

Olson Toward trophic treatment in parkinsonism: a primate step. Nature Med., 2:400–401(1996).

O'Rourke et al., "Postmitotic neurons migrate tangentially in the cortical ventricular zone," *Development* 124:997–1005, (1997).

Othberg et al., Specific effects of platelet derived growth factor (PDGF) on embryonic rat and human DA neurons in vitro. Exp. Brain Res., 105:111–122 (1995).

Panchinsion et al., Plasticity and stem cells in the vertebrate nervous system. *Curr. Opin. Cell Biol.* 10, 727–733 (1998).

Paulding and Czyzyk-Krzeska, Regulation of tyrosine hydroxylase mRNA stability by protein binding, pyrimidine-rich sequence in the 3'untranslated region. *J. Biol. Chem.* 274, 2532–2538 (1999).

Perez Velazquez et al., In vitro ischemia promotes glutamate-mediated free radical generation and intracellular calcium accumulation in hippocampal pyramidal neurons. *J. Neurosci.* 17, 9085–9094 (1997).

Potter et al., Enhancer-dependent expression of human k immunoglobulin genes introduced into mouse pre-B lymphocytes by electroporation, *Proc. Nat'l Acad Sci. USA,* 81:7161–7165, 1984.

Poulsen et al., TGFβ2 and TGFβ3 are potent survival factors for midbrain dopaminergic neurons. Neuron, 13:1245 (1994).

Rippe et al., DNA-mediated gene transfer into adult rat hepatocytes in primary culture, *Mol. Cell Biol.,* 10:689–695, 1990.

Rosenblad. Glial cell line-derived neurotrophic factor increases survival, growth and function of intrastriatal fetal nigral dopaminergic grafts. Neurosci. 75:979–985 (1996).

Rutka et al., Role of glial filaments in cells and tumors of glial origin: a review J Neurosurg.;87(3):420–30, (1997).

Sakanaka, et al. In vivo evidence that erythropoietin protects neurons from ischemic damage. *Proc. Natl. Acad. Sci.* 95,4635–4640(1998).

Sanberg et al., Cell transplantation for Huntington's disease R.G. Landes Co., Boca Raton, Fla., pp. 19–21, (1994).

Saucedo-Cardenas et al., Nurr1 is essential for the induction of the dopaminergic phenotype and the survival of ventral mesencephalic late dopaminergic precursor neurons. *Proc. Natl. Acad. Sci .* 95, 4013–4018, (1998).

Sauer et al., Glial cell line-derived neurotrophic factor but not transforming growth factor .beta.3 prevents delayed degeneration of nigral DA neurons following striatal 6-hydroxydopamine lesion. Proc. Natl. Acad. Sci. USA., 92:8935–8939(1994).

Scandurro and Beckman, Common proteins bind mRNAs encoding erythropoietin, tyrosine hydroxylase, and vascular endothelial growth factor. *Bioch. Biophys. Res. Comm.* 246, 436–440 (1998).

Schmidt et al., Functional activity of substantia nigra grafts reinnervating the striatum: neurotransmitter metabolism and [14C]2-deoxy-D-glucose autoradiography *J. Neurochem.* 38:737–748, (1982).

Shamim et al., Sequential roles for Fgf4, En1 and Fgf8 in specification and regionalisation of the midbrain. *Development* 126, 945–959 (1999).

Silver and Erecinska, Oxygen and ion concentrations in normoxic and hypoxic brain cells. In *Oxygen Transport to Tissue XX*, 7–15, edited by Hudetz and Bruley, Plenum Press, New York (1988).

Simone et al., En-1 and En-2 control the fate of the dopaminergic neurons in the substantia nigra and ventral tegmentum. *Eur. J. Neurosci.* 10, 389–399 (1998).

Smidt et al., A homeodomain gene Ptx 3 has highly restricted brain expression in mesencephalic dopaminergic neurons. *Proc. Natl. Acad. Sci.* 94, 13305–13310, (1997).

Stenevi et al., Transplantation of central and peripheral monoamine neurons to the adult rat brain: techniques and conditions for survival, *Brain Res.* 114:1–20 (1976)

Studer et al., Non-invasive dopamine determination by reversed phase HPLC in the medium of free-floating roller tube cultures of rat fetal ventral mesencephalon. A tool to assess dopaminergic tissue prior to grafting. *Brain Res. Bull.* 41, 143–150 (1996).

Studer et al., Transplantation of expanded mesencephalic precursors leads to recovery in parkinsonian rats. *Nature Neurosci.* 1, 290–295 (1998).

Tur-Kaspa et al., Use of electroporation to introduce biologically active foreign genes into primary rat hepatocytes, *Mol. Cell Biol,* 6:716–718, 1986

U.S. Pat. No. 5,082,670
U.S. Pat. No. 5,650,148
U.S. Pat. No. 5,762,926
U.S. Pat. No. 4,683,195
U.S. Pat. No. 4,800,159
U.S. Pat. No. 4,861,719
U.S. Pat. No. 4,886,741
U.S. Pat. No. 4,888,278
U.S. Pat. No. 5,019,034
U.S. Pat. No. 5,120,657
U.S. Pat. No. 5,139,941
U.S. Pat. No. 5,225,326
U.S. Pat. No. 5,252,479
U.S. Pat. No. 5,328,688
U.S. Pat. No. 5,364,790
U.S. Pat. No. 5,474,935
U.S. Pat. No. 5,506,098
U.S. Pat. No. 5,507,724
U.S. Pat. No. 5,521,061
U.S. Pat. No. 5,538,869
U.S. Pat. No. 5,585,362
U.S. Pat. No. 5,612,205
U.S. Pat. No. 5,612,205
U.S. Pat. No. 5,620,689
U.S. Pat. No. 5,622,856
U.S. Pat. No. 5,631,018
U.S. Pat. No. 5,658,776
U.S. Pat. No. 5,661,025
U.S. Pat. No. 5,661,033
U.S. Pat. No. 5,665,540
U.S. Pat. No. 5,670,488
U.S. Pat. No. 5,686,278
U.S. Pat. No. 5,693,509
U.S. Pat. No. 5,707,618
U.S. Pat. No. 5,714,166
U.S. Pat. No. 5,721,367
U.S. Pat. No. 5,749,847
U.S. Pat. No. 5,750,376
U.S. Pat. No. 5,770,414
U.S. Pat. No. 5,773,289
U.S. Pat. No. 5,785,987
U.S. Pat. No. 5,789,213
U.S. Pat. No. 5,789,215
U.S. Pat. No. 5,789,390
U.S. Pat. No. 5,795,581
U.S. Pat. No. 5,800,992
U.S. Pat. No. 5,824,544
U.S. Pat. No. 5,824,547
U.S. Pat. No. 5,827,703
U.S. Pat. No. 5,830,698
U.S. Pat. No. 5,830,725
U.S. Pat. No. 5,830,727
U.S. Pat. No. 5,834,181
U.S. Pat. No. 5,834,441
U.S. Pat. No. 5,836,905
U.S. Pat. No. 5,849,571
U.S. Pat. No. 5,851,521
U.S. Pat. No. 5,851,818
U.S. Pat. No. 5,855,910
U.S. Pat. No. 5,856,152
U.S. Pat. No. 5,861,314
U.S. Pat. No. 5,863,541
U.S. Pat. No. 5,869,326
U.S. Pat. No. 5,879,934
U.S. Pat. No. 5,888,502

Ungerstedt and Arbuthnott, Quantitative recording of rotational behavior in rats after 6-hydroxy-dopamine lesions of the nigrostriatal dopamine system. *Brain Res.* 24:485–493, (1970).

Wang et al., Induction of dopaminergic neuron phenotype in the midbrain by Sonic hedgehog protein. *Nature Med.* 1, 1184–1188 (1995).

Wictorin et al., Reformation of long axon pathways in adult rat CNS by human forebrain neuroblasts. *Nature,* 347:556–558 (1990).

Wu and Wu, "Evidence for targeted gene delivery to HepG2 hepatoma cells in vitro," *Biochemistry,* 27:887–892, (1988).

Wu and Wu, Receptor-mediated in vitro gene transfections by a soluble DNA carrier system, *J. Biol. Chem.,* 262:4429–4432, (1987).

Wurst et al., Multiple developmental defects in Engrailed-1 mutant mice: An early mid-hindbrain deletion and patterning defects in forelimbs and sternum. *Development* 120, 2065–2075 (1994).

Yamada et al., Control of cell pattern in the developing nervous system: polarizing activity of the floor plate and notochord. *Cell* 64, 635–647, (1991).

Yang et al., "In vivo and in vitro gene transfer to mammalian somatic cells by particle bombardment," Proc. Nat'l Acad. Sci. USA, 87:9568–9572, 1990.

Ye et al., FGF and Shh signals control dopaminergic and serotonergic cell fate in the anterior neural plate. *Cell* 93,755–766 (1998).

Yoshimoto et al., Astrocytes retrovirally transduced with BDNF elicit behavioral improvement in a rat model of Parkinson's disease. Brain Res., 691:25–36, (1995).

What is claimed is:

1. A method of increasing cell differentiation of undifferentiated mesencephalic precursor cells comprising:
   (a) culturing undifferentiated mesencephalic precursor cells in low ambient oxygen conditions between about 1% to about 5% oxygen, wherein said low ambient oxygen conditions increase the cellular differentiation of said mesencephalic precursor cells into dopaminergic neurons as compared to a similar mesencephalic precursor cell population that is grown in 20% oxygen incubator conditions, and
   (b) determining the differentiation specific phenotype of said mesencephalic precursor cells by monitoring the message level for tyrosine hydroxylase (TH), Ptx-3, Engrailed-1 (En1), or fibroblast growth factor 8b (FGF8b) wherein an increase in TH, Ptx-3, En1 or FGF8b message level indicates the differentiation of said mesencephalic precursor cells.

2. The method of claim 1, wherein said low ambient oxygen conditions mimic physiological oxygen conditions for said mesencephalic precursor cells.

3. The method of claim 1, wherein said mesencephalic precursor cells are primary tissue culture cells.

4. The method of claim 1, wherein said mesencephalic precursor cells are derived from a cell line.

5. The method of claim 1, wherein said mesencephalic precursor cells are fetal cells.

6. The method of claim 1, wherein said message level is monitored using PCR™, in situ hybridization, RNAse protection assay, or single cell PCR™.

7. The method of claim 1, wherein said low ambient oxygen conditions produce a cell population that is depleted in GABAnergic neurons (gamma-aminobutyric acid neurons) as compared to a similar cell population that is grown in 20% oxygen conditions.

8. The method of claim 1, further comprising growing said mesencephalic precursor cells in the presence of a neuronal growth stimulant, mitogen, cytokine, neuroprotective factor, or anti-apoptotic agent.

9. The method of claim 1, wherein the cellular differentiation phenotype is retained after transfer of said mesencephalic precursor cells from said low ambient oxygen conditions to 20% oxygen conditions.

10. The method of claim 9, wherein said mesencephalic precursor cells are grown in low ambient oxygen conditions for multiple generations prior to transfer to 20% oxygen culture conditions.

11. The method of claim 1, wherein said mesencephalic precursor cells are continuously maintained in low ambient culture conditions.

* * * * *

SEQUENCE LISTING

<160> NUMBER OF SEQ ID NOS: 24

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:Forward PCR
      primer for GAPDH

<400> SEQUENCE: 1
ctcgtctcat agacaagatg gtgaag                                              26

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:Reverse PCR
      primer for GAPDH

<400> SEQUENCE: 2
agactccacg acatactcag cacc                                                24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Forward PCR
      primer for VHL

<400> SEQUENCE: 3
cctctcaggt catcttctgc aacc                                                24

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Reverse PCR
      primer for VHL

<400> SEQUENCE: 4
agggatggca caaacagttc c                                                   21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:Forward PCR
      primer for HIF1a

<400> SEQUENCE: 5
gcagcacgat ctcggcgaag caaa                                                24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:Reverse PCR
      primer for HIF1a

<400> SEQUENCE: 6

```
gcaccataac aaagccatcc aggg                                              24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:Forward PCR
      primer for EPO

<400> SEQUENCE: 7
cgctccccca cgcctcattt g                                                 21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:Reverse PCR
      primer for EPO

<400> SEQUENCE: 8
agcggcttgg gtggcgtctg ga                                                22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:Forward PCR
      primer for VEGF

<400> SEQUENCE: 9
gtgcactgga ccctggcttt act                                               23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:Reverse PCR
      primer for VEGF

<400> SEQUENCE: 10
cgccttgcaa cgcgagtctg tgtt                                              24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:Forward PCR
      primer for Nurr1

<400> SEQUENCE: 11
tgaagagagc ggagaaggag atc                                               23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Reverse PCR
      primer for Nurr1

<400> SEQUENCE: 12
```
tctggagtta agaaatcgga gctg                                    24

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:Forward PCR
      primer for Ptx3

<400> SEQUENCE: 13
cgtgcgtggt tggttcaaga ac                                      22

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Reverse PCR
      primer for Ptx3H

<400> SEQUENCE: 14
gcggtgagaa tacaggttgt gaag                                    24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:Forward PCR
      primer for SHH

<400> SEQUENCE: 15
ggaagatcac aagaaactcc gaac                                    24

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:Reverse PCR
      primer for SHH

<400> SEQUENCE: 16
ggatgcgagc tttggattca tag                                     23

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:Forward PCR
      primer for FGF8

<400> SEQUENCE: 17
catgtgaggg accagagcc                                          19

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:Reverse PCR
      primer for FGF8

<400> SEQUENCE: 18
gtagttgttc tccagcagga tc                                      22

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:Forward PCR
      primer for En1

<400> SEQUENCE: 19
tcaagactga ctacagcaac ccc                                             23

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:Reverse PCR
      primer for En1

<400> SEQUENCE: 20
ctttgtcctg aaccgtggtg gtag                                            24

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:Forward  PCR
      primer for FGFR3

<400> SEQUENCE: 21
atcctcggga gatgacgaag ac                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:Reverse PCR
      primer for FGFR3

<400> SEQUENCE: 22
ggatgctgcc aaacttgttc tc                                              22

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:Forward  PCR
      primer for BDNF

<400> SEQUENCE: 23
gtgacagtat tagcgagtgg g                                               21

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence:Reverse PCR
      primer for BDNF

<400> SEQUENCE: 24
gggtagttcg gcattgc                                                    17